(12) United States Patent
Seyedsayamdost et al.

(10) Patent No.: US 11,629,174 B2
(45) Date of Patent: Apr. 18, 2023

(54) CRYPTIC METABOLITES AND METHOD FOR ACTIVATING SILENT BIOSYNTHETIC GENE CLUSTERS IN ACTINOMYCETE BACTERIA

(71) Applicant: The Trustees of Princeton University, Princeton, NJ (US)

(72) Inventors: Mohammad R. Seyedsayamdost, Princeton, NJ (US); Fei Xu, Princeton, NJ (US); Kyuho Moon, Princeton, NJ (US); Behnam Nazari, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 497 days.

(21) Appl. No.: 16/610,330

(22) PCT Filed: May 11, 2018

(86) PCT No.: PCT/US2018/032340
§ 371 (c)(1),
(2) Date: Nov. 1, 2019

(87) PCT Pub. No.: WO2018/209249
PCT Pub. Date: Nov. 15, 2018

(65) Prior Publication Data
US 2020/0079823 A1     Mar. 12, 2020

Related U.S. Application Data

(60) Provisional application No. 62/504,603, filed on May 11, 2017.

(51) Int. Cl.
| | | |
|---|---|---|
| C07K 14/36 | (2006.01) | |
| C07K 7/64 | (2006.01) | |
| C12N 1/20 | (2006.01) | |
| C12N 1/38 | (2006.01) | |
| G01N 33/50 | (2006.01) | |
| C12Q 1/02 | (2006.01) | |
| A61K 38/00 | (2006.01) | |

(52) U.S. Cl.
CPC ............... *C07K 14/36* (2013.01); *C07K 7/64* (2013.01); *C12N 1/20* (2013.01); *C12N 1/38* (2013.01); *C12Q 1/025* (2013.01); *G01N 33/5044* (2013.01); *A61K 38/00* (2013.01)

(58) Field of Classification Search
None
See application file for complete search history.

(56) References Cited

U.S. PATENT DOCUMENTS 8,609,342 B2    12/2013   Iida et al.
2006/0064770 A1    3/2006   Frendewey et al.
2008/0268501 A1    10/2008   Chater et al.

FOREIGN PATENT DOCUMENTS

WO    WO-2015138442 A1 *   9/2015  ............. C12N 15/52

OTHER PUBLICATIONS

Gardiner, Donald M., Kemal Kazan, and John M. Manners. "Nutrient profiling reveals potent inducers of trichothecene biosynthesis in Fusarium graminearum." Fungal genetics and biology 46.8 (2009): 604-613. (Year: 2009).*
Thorne, Natasha, Douglas S. Auld, and James Inglese. "Apparent activity in high-throughput screening: origins of compound-dependent assay interference." Current opinion in chemical biology 14.3 (2010): 315-324. (Year: 2010).*
Seipke, Ryan F. "Strain-level diversity of secondary metabolism in Streptomyces albus." PLoS One 10.1 (2015): e0116457. (Year: 2015).*
Genové, Guillem, Benjamin S. Glick, and Alison L. Barth. "Brighter reporter genes from multimerized fluorescent proteins." Biotechniques 39.6 (2005): 814-822. (Year: 2005).*
International Search Report and Written Opinion for PCT/US2018/032340, dated Oct. 30, 2018.
Takada et al. "Surugamides A-E, Cyclic Octapeptides with Four D-Amino Acid Residues, from a Marine *Streptomyces* sp.:LC-MS-Aided Inspection of Partial Hydrolysates for the Distinction of D- and L-Amino Acid Residues in the Sequence," The Journal of Organic Chemistry,Jun. 7, 2013 (Jun. 7, 2013), vol. 78, Iss.13, pp. 6476-6780.
Reen et al. "The Sound of Silence: Activating Silent Biosynthetic Gene Clusters in Marine Microorganisms," Marine Drugs, Jul. 31, 2015 (Jul. 31, 2015), vol. 13, Iss. 8, pp. 4754-4783.
Olano C. et al. "Activation and identification of five clusters for secondary metabolites in Streptomyces albus J1074", Microbial Biotechnology published by John Wiley & Sons Ltd and Society for Applied Microbiology, 2014.
Sun, J. et al. "Green fluorescent protein as a reporter for spatial and temporal gene expression in Streptomyces coelicolor A3(2)", Microbiology, vol. 145, pp. 2221-2227, 1999.

(Continued)

Primary Examiner — Robert J Yamasaki
(74) Attorney, Agent, or Firm — Meagher Emanuel Laks Goldberg & Lian, LLP

(57) ABSTRACT

Disclosed is a high-throughput transcriptional assay format in Actinomycete bacteria, and *Streptomyces* spp. in particular, that leverages eGFP, inserted both at a neutral site and inside the biosynthetic cluster of interest, as a read-out for secondary metabolite synthesis. Using this approach, a silent gene cluster in *Streptomyces albus* J1074 was induced. The cytotoxins etoposide and ivermectin were revealed as potent inducers, allowing the isolation and structural characterization of nearly 20 novel small molecule products of the chosen cluster. One of these molecules is a novel antifungal, while several others inhibit a cysteine protease implicated in cancer. Studies addressing the mechanism of induction by the two elicitors led to the identification of a pathway-specific transcriptional repressor that silences the gene cluster under normal growth conditions. The successful implementation of this approach will allow future discovery of cryptic metabolites with useful bioactivities from Actinomycete bacteria.

9 Claims, 23 Drawing Sheets
Specification includes a Sequence Listing.

(56) References Cited

OTHER PUBLICATIONS

Takada, K. et al. "Surugamides A-E, Cyclic Octapeptides with Four D-Amino Acid Residues, from a Marine *Streptomyces* sp.: LC-MS-Aided Inspection of Partial Hydrolysates for the Distinction of D- and L-Amino Acid Residues in the Sequence", JOC, The Journal of Organic Chemistry, vol. 78, pp. 6746-6750, 2013.
Hawas, U. et al. "Mansouramycins A-D, Cytotoxic Isoquinolinequinones from a Marine Streptomycete", J. Nat. Prod. vol. 72, pp. 2120-2124, 2009.
Rigali, S. et al. "Extending the classification of bacterial transcription factors beyond the helix-turn-helix motif as an alternative approach to discover new cis/trans relationships", Nucleic Acids Research, vol. 32, No. 11, pp. 3418-3426, 2004.
Van Wezel, G. et al. "The regulation of the secondary metabolism of Streptomyces: new links and experimental advances", Nat. Prod. Rep., vol. 28, pp. 1311-1333, 2011.

\* cited by examiner

10

- 20: Provide An Actinomycete Bacterial Cell
- 30: Expose Cell To Test Compounds
- 40: Measuring First Expression Of Reporter Gene
- 50: Measuring Second Expression Of Reporter Gene
- 60: Identifying Gene Cluster Activation

FIG. 1

| Assays | 11 | 12 | 13 | 14 | 15 | 16 | 18 | 23 | 24 |
|---|---|---|---|---|---|---|---|---|---|
| Cathepsin B Inhibition | >100 | 12.4 | 9 | >100 | 42.3 | 68.3 | >100 | >100 | N.D |
| Staphylococcus aureus Newman | >100 | N.D.[a] | N.D. | >100 | 27.4 | >100 | N.D. | >100 | >100 |
| Bacillus subtilis 168 | >100 | N.D. | N.D. | >100 | 21.7 | >100 | N.D. | >100 | >100 |
| Enterococcus faecalis OG1RF | >100 | N.D. | N.D. | >100 | >100 | >100 | N.D. | >100 | >100 |
| Saccharomyces cerecisiae | >100 | N.D. | N.D. | >100 | 3.5 | >100 | N.D. | >100 | >100 |
| Saccharomyces pombe | >100 | N.D. | N.D. | >100 | 32.5 | >100 | N.D. | >100 | >100 |
| E. coli K12 | >100 | N.D. | N.D. | >100 | >100 | >100 | N.D. | >100 | >100 |
| Pseudomonas aeruginosa PAO1 | >100 | N.D. | N.D. | >100 | >100 | >100 | N.D. | >100 | >100 |

FIG. 8

[a]N.D.; not determined

SEQUENCE LISTING

```
<160> NUMBER OF SEQ ID NOS: 46

<210> SEQ ID NO 1
<211> LENGTH: 29
<212> TYPE: PRT
<213> ORGANISM: Artificial Sequence
<220> FEATURE:
<223> OTHER INFORMATION: Primer Sequence

<400> SEQUENCE: 1

Ala Ala Gly Cys Thr Thr Ala Gly Ala Cys Gly Ala Cys Cys Ala Cys
1               5                   10                  15

Cys Thr Thr Cys Gly Cys Cys Gly Thr Cys Thr Gly Cys
            20                  25

<210> SEQ ID NO 2
<211> LENGTH: 30
<212> TYPE: PRT
<213> ORGANISM: Artificial Sequence
<220> FEATURE:
<223> OTHER INFORMATION: Primer Sequence

<400> SEQUENCE: 2

Ala Ala Gly Cys Thr Thr Thr Ala Gly Ala Cys Gly Gly Ala Cys Gly
1               5                   10                  15

Gly Gly Ala Cys Gly Gly Cys Gly Thr Gly Cys Ala Gly Cys
            20                  25                  30

<210> SEQ ID NO 3
```

```
<211> LENGTH: 30
<212> TYPE: PRT
<213> ORGANISM: Artificial Sequence
<220> FEATURE:
<223> OTHER INFORMATION: Primer Sequence

<400> SEQUENCE: 3

Ala Ala Gly Cys Thr Thr Ala Cys Gly Ala Cys Cys Cys Thr
1               5                   10                  15

Gly Cys Gly Gly Ala Cys Cys Gly Thr Cys Thr Thr Cys Cys
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Primer Sequence

<400> SEQUENCE: 4

Ala Ala Gly Cys Thr Thr Thr Cys Gly Thr Gly Cys Ala Cys Cys Ala
1               5                   10                  15

Cys Cys Thr Gly Cys Ala Cys Cys Gly Gly Cys Thr Gly Cys
            20                  25                  30

<210> SEQ ID NO 5
<211> LENGTH: 60
<212> TYPE: PRT
<213> ORGANISM: Artificial Sequence
<220> FEATURE:
<223> OTHER INFORMATION: Primer Sequence

<400> SEQUENCE: 5

Thr Thr Cys Thr Thr Cys Gly Thr Cys Ala Ala Cys Ala Cys Cys Cys
1               5                   10                  15

Thr Gly Gly Thr Gly Cys Thr Gly Cys Gly Gly Cys Ala Gly Cys Ala
            20                  25                  30

Gly Gly Thr Gly Cys Cys Gly Gly Ala Thr Thr Cys Cys Gly Gly Gly
        35                  40                  45

Gly Ala Thr Cys Cys Gly Thr Cys Gly Ala Cys Cys
        50                  55                  60

<210> SEQ ID NO 6
<211> LENGTH: 60
<212> TYPE: PRT
<213> ORGANISM: Artificial Sequence
<220> FEATURE:
<223> OTHER INFORMATION: Primer Sequence

<400> SEQUENCE: 6

Gly Ala Cys Cys Gly Gly Gly Thr Gly Thr Cys Gly Gly Thr
1               5                   10                  15

Ala Gly Gly Cys Thr Gly Ala Gly Gly Ala Thr Gly Thr Cys Gly Thr
            20                  25                  30

Gly Gly Gly Cys Gly Ala Thr Cys Thr Thr Gly Thr Ala Gly Gly Cys
        35                  40                  45

Thr Gly Gly Ala Gly Cys Thr Gly Cys Thr Thr Cys
        50                  55                  60

<210> SEQ ID NO 7
<211> LENGTH: 60
<212> TYPE: PRT
<213> ORGANISM: Artificial Sequence
```

<220> FEATURE:
<223> OTHER INFORMATION: Primer Sequence

<400> SEQUENCE: 7

Ala Gly Ala Thr Cys Ala Gly Cys Cys Ala Cys Ala Cys Cys Cys Thr
1               5                   10                  15

Gly Ala Thr Cys Cys Gly Cys Cys Gly Ala Cys Gly Gly Thr Cys
                20                  25                  30

Cys Thr Cys Gly Cys Cys Ala Gly Ala Thr Thr Cys Cys Gly Gly Gly
            35                  40                  45

Gly Ala Thr Cys Cys Gly Thr Cys Gly Ala Cys Cys
        50                  55                  60

<210> SEQ ID NO 8
<211> LENGTH: 60
<212> TYPE: PRT
<213> ORGANISM: Artificial Sequence
<220> FEATURE:
<223> OTHER INFORMATION: Primer Sequence

<400> SEQUENCE: 8

Cys Gly Ala Gly Gly Cys Thr Gly Ala Ala Gly Ala Ala Gly Thr Thr
1               5                   10                  15

Gly Thr Cys Cys Cys Gly Gly Gly Thr Gly Cys Cys Gly Ala Cys Ala
                20                  25                  30

Cys Gly Thr Thr Cys Ala Cys Thr Gly Thr Ala Gly Gly Cys
            35                  40                  45

Thr Gly Gly Ala Gly Cys Thr Gly Cys Thr Thr Cys
        50                  55                  60

<210> SEQ ID NO 9
<211> LENGTH: 31
<212> TYPE: PRT
<213> ORGANISM: Artificial Sequence
<220> FEATURE:
<223> OTHER INFORMATION: Primer Sequence

<400> SEQUENCE: 9

Ala Cys Thr Cys Thr Ala Gly Ala Cys Thr Gly Ala Ala Gly Thr Thr
1               5                   10                  15

Cys Thr Cys Cys Gly Gly Gly Cys Cys Ala Cys Gly Ala Cys
                20                  25                  30

<210> SEQ ID NO 10
<211> LENGTH: 51
<212> TYPE: PRT
<213> ORGANISM: Artificial Sequence
<220> FEATURE:
<223> OTHER INFORMATION: Primer Sequence

<400> SEQUENCE: 10

Gly Thr Cys Gly Thr Ala Cys Gly Gly Thr Cys Ala Cys Cys Ala Thr
1               5                   10                  15

Cys Cys Thr Cys Thr Ala Gly Thr Cys Ala Ala Gly Cys Thr Thr Gly
                20                  25                  30

Cys Ala Cys Ala Gly Cys Thr Thr Cys Ala Ala Thr Cys Thr Ala Thr
            35                  40                  45

Cys Thr Gly
        50

<210> SEQ ID NO 11

```
<211> LENGTH: 32
<212> TYPE: PRT
<213> ORGANISM: Artificial Sequence
<220> FEATURE:
<223> OTHER INFORMATION: Primer Sequence

<400> SEQUENCE: 11

Cys Ala Ala Gly Cys Thr Thr Gly Ala Cys Thr Ala Gly Ala Gly Gly
1               5                   10                  15

Ala Thr Gly Gly Thr Gly Ala Cys Cys Gly Thr Ala Cys Gly Ala Cys
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Primer Sequence

<400> SEQUENCE: 12

Gly Cys Thr Cys Thr Ala Gly Ala Thr Gly Cys Thr Cys Gly Cys
1               5                   10                  15

Cys Thr Gly Cys Cys Thr Cys Ala Cys Cys Ala Gly Ala Cys Thr Cys
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Primer Sequence

<400> SEQUENCE: 13

Ala Gly Thr Ala Ala Gly Cys Thr Thr Cys Cys Ala Cys Gly Ala
1               5                   10                  15

Cys Thr Ala Thr Thr Thr Gly Cys Ala Ala Cys Ala Gly Thr
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Primer Sequence

<400> SEQUENCE: 14

Ala Cys Cys Ala Ala Gly Cys Thr Thr Cys Gly Gly Gly Gly Thr Cys
1               5                   10                  15

Ala Thr Thr Ala Thr Ala Gly Cys Gly Ala Thr Thr Thr Thr
            20                  25                  30

<210> SEQ ID NO 15
<211> LENGTH: 21
<212> TYPE: PRT
<213> ORGANISM: Artificial Sequence
<220> FEATURE:
<223> OTHER INFORMATION: Primer Sequence

<400> SEQUENCE: 15

Ala Thr Cys Ala Thr Cys Ala Cys Gly Cys Gly Cys Gly Ala Gly Cys
1               5                   10                  15

Thr Gly Ala Gly Cys
            20
```

-continued

```
<210> SEQ ID NO 16
<211> LENGTH: 18
<212> TYPE: PRT
<213> ORGANISM: Artificial Sequence
<220> FEATURE:
<223> OTHER INFORMATION: Primer Sequence

<400> SEQUENCE: 16

Cys Gly Ala Gly Gly Ala Cys Gly Ala Gly Gly Ala Gly Thr Thr Thr
1               5                   10                  15

Cys Gly

<210> SEQ ID NO 17
<211> LENGTH: 21
<212> TYPE: PRT
<213> ORGANISM: Artificial Sequence
<220> FEATURE:
<223> OTHER INFORMATION: Primer Sequence

<400> SEQUENCE: 17

Ala Gly Ala Thr Cys Ala Gly Cys Cys Ala Cys Ala Cys Cys Cys Thr
1               5                   10                  15

Gly Ala Thr Cys Cys
            20

<210> SEQ ID NO 18
<211> LENGTH: 21
<212> TYPE: PRT
<213> ORGANISM: Artificial Sequence
<220> FEATURE:
<223> OTHER INFORMATION: Primer Sequence

<400> SEQUENCE: 18

Thr Gly Ala Ala Gly Ala Ala Gly Thr Thr Gly Thr Cys Cys Cys Gly
1               5                   10                  15

Gly Gly Thr Gly Cys
            20

<210> SEQ ID NO 19
<211> LENGTH: 28
<212> TYPE: PRT
<213> ORGANISM: Artificial Sequence
<220> FEATURE:
<223> OTHER INFORMATION: Primer Sequence

<400> SEQUENCE: 19

Gly Gly Ala Thr Cys Cys Ala Thr Cys Ala Gly Thr Gly Cys Cys Ala
1               5                   10                  15

Thr Gly Gly Gly Gly Ala Gly Cys Thr Thr Cys Cys
            20                  25

<210> SEQ ID NO 20
<211> LENGTH: 32
<212> TYPE: PRT
<213> ORGANISM: Artificial Sequence
<220> FEATURE:
<223> OTHER INFORMATION: Primer Sequence

<400> SEQUENCE: 20

Thr Thr Gly Cys Thr Cys Ala Cys Cys Ala Thr Thr Gly Cys Gly Thr
1               5                   10                  15

Cys Cys Cys Cys Thr Gly Cys Gly Cys Cys Ala Cys Thr Gly Cys
            20                  25                  30
```

```
<210> SEQ ID NO 21
<211> LENGTH: 27
<212> TYPE: PRT
<213> ORGANISM: Artificial Sequence
<220> FEATURE:
<223> OTHER INFORMATION: Primer Sequence

<400> SEQUENCE: 21

Gly Ala Ala Thr Thr Cys Ala Thr Gly Thr Cys Ala Gly Gly
1               5                   10                  15

Ala Thr Gly Ala Gly Cys Gly Gly Thr Cys Gly
            20                  25

<210> SEQ ID NO 22
<211> LENGTH: 30
<212> TYPE: PRT
<213> ORGANISM: Artificial Sequence
<220> FEATURE:
<223> OTHER INFORMATION: Primer Sequence

<400> SEQUENCE: 22

Ala Ala Gly Cys Thr Thr Thr Cys Cys Ala Gly Gly Ala Ala Cys Cys
1               5                   10                  15

Ala Gly Ala Gly Cys Cys Gly Thr Thr Cys Cys Thr Gly Cys
            20                  25                  30

<210> SEQ ID NO 23
<211> LENGTH: 29
<212> TYPE: PRT
<213> ORGANISM: Artificial Sequence
<220> FEATURE:
<223> OTHER INFORMATION: Primer Sequence

<400> SEQUENCE: 23

Ala Gly Gly Gly Gly Ala Cys Gly Cys Ala Ala Thr Gly Gly Thr Gly
1               5                   10                  15

Ala Gly Cys Ala Ala Gly Gly Gly Cys Gly Ala Gly Gly
            20                  25

<210> SEQ ID NO 24
<211> LENGTH: 28
<212> TYPE: PRT
<213> ORGANISM: Artificial Sequence
<220> FEATURE:
<223> OTHER INFORMATION: Primer Sequence

<400> SEQUENCE: 24

Gly Ala Ala Thr Thr Cys Thr Cys Ala Cys Thr Thr Gly Thr Ala Cys
1               5                   10                  15

Ala Gly Cys Thr Cys Gly Thr Cys Cys Ala Thr Gly
            20                  25

<210> SEQ ID NO 25
<211> LENGTH: 21
<212> TYPE: PRT
<213> ORGANISM: Artificial Sequence
<220> FEATURE:
<223> OTHER INFORMATION: Primer Sequence

<400> SEQUENCE: 25

Thr Thr Thr Cys Cys Gly Cys Thr Gly Cys Thr Gly Cys Thr Gly Ala
1               5                   10                  15

Ala Gly Cys Th

<210> SEQ ID NO 26
<211> LENGTH: 21
<212> TYPE: PRT
<213> ORGANISM: Artificial Sequence
<220> FEATURE:
<223> OTHER INFORMATION: Primer Sequence

<400> SEQUENCE: 26

Thr Cys Gly Ala Gly Thr Thr Cys Gly Cys Gly Gly Thr Ala Gly Gly
1               5                   10                  15

Thr Cys Ala Gly Gly
            20

<210> SEQ ID NO 27
<211> LENGTH: 29
<212> TYPE: PRT
<213> ORGANISM: Artificial Sequence
<220> FEATURE:
<223> OTHER INFORMATION: Primer Sequence

<400> SEQUENCE: 27

Thr Thr Gly Cys Thr Cys Ala Cys Ala Thr Thr Gly Cys Gly Thr
1               5                   10                  15

Cys Cys Cys Cys Thr Gly Cys Gly Cys Cys Ala Cys
            20                  25

<210> SEQ ID NO 28
<211> LENGTH: 28
<212> TYPE: PRT
<213> ORGANISM: Artificial Sequence
<220> FEATURE:
<223> OTHER INFORMATION: Primer Sequence

<400> SEQUENCE: 28

Ala Gly Gly Gly Gly Ala Cys Gly Cys Ala Ala Thr Gly Gly Thr Gly
1               5                   10                  15

Ala Gly Cys Met Gly Gly Gly Cys Gly Ala Gly Gly
            20                  25

<210> SEQ ID NO 29
<211> LENGTH: 29
<212> TYPE: PRT
<213> ORGANISM: Artificial Sequence
<220> FEATURE:
<223> OTHER INFORMATION: Primer Sequence

<400> SEQUENCE: 29

Ala Thr Cys Ala Thr Ala Thr Gly Ala Thr Gly Gly Thr Gly Ala Gly
1               5                   10                  15

Cys Ala Ala Gly Gly Gly Cys Gly Ala Gly Gly Ala Gly
            20                  25

<210> SEQ ID NO 30
<211> LENGTH: 30
<212> TYPE: PRT
<213> ORGANISM: Artificial Sequence
<220> FEATURE:
<223> OTHER INFORMATION: Primer Sequence

<400> SEQUENCE: 30

Ala Ala Gly Ala Ala Thr Thr Cys Thr Cys Ala Cys Thr Thr Gly Thr
1               5                   10                  15

Ala Cys Ala Gly Cys Thr Cys Gly Thr Cys Cys Ala Thr Gly
            20                  25                  30

<210> SEQ ID NO 31
<211> LENGTH: 48
<212> TYPE: PRT
<213> ORGANISM: Artificial Sequence
<220> FEATURE:
<223> OTHER INFORMATION: Primer Sequence

<400> SEQUENCE: 31

Ala Cys Ala Ala Thr Thr Gly Cys Ala Gly Cys Thr Cys Ala Ala Gly
1               5                   10                  15

Gly Ala Gly Gly Ala Thr Cys Cys Ala Thr Cys Ala Thr Gly Gly Thr
                20                  25                  30

Gly Ala Gly Cys Ala Ala Gly Gly Cys Gly Ala Gly Gly Ala Gly Gly
            35                  40                  45

<210> SEQ ID NO 32
<211> LENGTH: 30
<212> TYPE: PRT
<213> ORGANISM: Artificial Sequence
<220> FEATURE:
<223> OTHER INFORMATION: Primer Sequence

<400> SEQUENCE: 32

Ala Ala Gly Ala Ala Thr Thr Cys Thr Cys Ala Cys Thr Thr Gly Thr
1               5                   10                  15

Ala Cys Ala Gly Cys Thr Cys Gly Thr Cys Cys Ala Thr Gly
                20                  25                  30

<210> SEQ ID NO 33
<211> LENGTH: 28
<212> TYPE: PRT
<213> ORGANISM: Artificial Sequence
<220> FEATURE:
<223> OTHER INFORMATION: Primer Sequence

<400> SEQUENCE: 33

Ala Thr Ala Ala Gly Cys Thr Thr Ala Thr Gly Ala Ala Cys Ala Ala
1               5                   10                  15

Ala Gly Gly Thr Gly Thr Ala Ala Thr Gly Cys Gly
                20                  25

<210> SEQ ID NO 34
<211> LENGTH: 27
<212> TYPE: PRT
<213> ORGANISM: Artificial Sequence
<220> FEATURE:
<223> OTHER INFORMATION: Primer Sequence

<400> SEQUENCE: 34

Ala Ala Thr Cys Thr Ala Gly Ala Thr Cys Ala Gly Gly Thr Cys Ala
1               5                   10                  15

Gly Cys Ala Cys Gly Gly Thr Cys Ala Thr Gly
                20                  25

<210> SEQ ID NO 35
<211> LENGTH: 29
<212> TYPE: PRT
<213> ORGANISM: Artificial Sequence
<220> FEATURE:
<223> OTHER INFORMATION: Primer Sequence

<400> SEQUENCE: 35

Gly Cys Thr Thr Cys Thr Ala Gly Ala Gly Gly Gly Cys Gly Cys Gly

```
1               5                   10                  15
Cys Thr Gly Cys Thr Cys Ala Ala Cys Gly Thr Gly Ala
            20                  25

<210> SEQ ID NO 36
<211> LENGTH: 31
<212> TYPE: PRT
<213> ORGANISM: Artificial Sequence
<220> FEATURE:
<223> OTHER INFORMATION: Primer Sequence

<400> SEQUENCE: 36

Ala Cys Ala Ala Gly Cys Thr Thr Gly Cys Gly Thr Cys Cys Cys
1               5                   10                  15

Thr Cys Cys Gly Cys Cys Cys Ala Gly Thr Gly Cys Ala Ala Cys
            20                  25                  30

<210> SEQ ID NO 37
<211> LENGTH: 28
<212> TYPE: PRT
<213> ORGANISM: Artificial Sequence
<220> FEATURE:
<223> OTHER INFORMATION: Primer Sequence

<400> SEQUENCE: 37

Ala Thr Cys Ala Thr Ala Thr Gly Ala Thr Gly Ala Ala Ala Ala
1               5                   10                  15

Ala Gly Gly Ala Gly Thr Thr Ala Thr Gly Cys Gly
            20                  25

<210> SEQ ID NO 38
<211> LENGTH: 27
<212> TYPE: PRT
<213> ORGANISM: Artificial Sequence
<220> FEATURE:
<223> OTHER INFORMATION: Primer Sequence

<400> SEQUENCE: 38

Ala Ala Gly Ala Ala Thr Thr Cys Thr Cys Ala Gly Gly Thr Cys Ala
1               5                   10                  15

Gly Cys Ala Cys Gly Gly Thr Cys Ala Thr Gly
            20                  25

<210> SEQ ID NO 39
<211> LENGTH: 20
<212> TYPE: PRT
<213> ORGANISM: Artificial Sequence
<220> FEATURE:
<223> OTHER INFORMATION: Primer Sequence

<400> SEQUENCE: 39

Cys Ala Ala Gly Ala Cys Cys Gly Thr Cys Ala Ala Gly Gly Thr Gly
1               5                   10                  15

Cys Thr Cys Thr
            20

<210> SEQ ID NO 40
<211> LENGTH: 20
<212> TYPE: PRT
<213> ORGANISM: Artificial Sequence
<220> FEATURE:
<223> OTHER INFORMATION: Primer Sequence

<400> SEQUENCE: 40
```

```
Gly Ala Gly Cys Cys Gly Ala Gly Ala Thr Gly Ala Thr Gly Ala Cys
1               5                   10                  15

Cys Thr Thr Cys
            20
```

<210> SEQ ID NO 41
<211> LENGTH: 20
<212> TYPE: PRT
<213> ORGANISM: Artificial Sequence
<220> FEATURE:
<223> OTHER INFORMATION: Primer Sequence

<400> SEQUENCE: 41

```
Gly Ala Gly Ala Ala Cys Thr Ala Cys Cys Gly Gly Ala Cys Ala
1               5                   10                  15

Ala Cys Gly Ala
            20
```

<210> SEQ ID NO 42
<211> LENGTH: 20
<212> TYPE: PRT
<213> ORGANISM: Artificial Sequence
<220> FEATURE:
<223> OTHER INFORMATION: Primer Sequence

<400> SEQUENCE: 42

```
Gly Gly Gly Thr Cys Gly Thr Ala Gly Gly Ala Gly Ala Gly Gly Thr
1               5                   10                  15

Cys Cys Ala Gly
            20
```

<210> SEQ ID NO 43
<211> LENGTH: 20
<212> TYPE: PRT
<213> ORGANISM: Artificial Sequence
<220> FEATURE:
<223> OTHER INFORMATION: Primer Sequence

<400> SEQUENCE: 43

```
Gly Ala Cys Gly Ala Gly Ala Cys Cys Cys Thr Gly Thr Cys Thr Thr
1               5                   10                  15

Ala Cys Gly Cys
            20
```

<210> SEQ ID NO 44
<211> LENGTH: 20
<212> TYPE: PRT
<213> ORGANISM: Artificial Sequence
<220> FEATURE:
<223> OTHER INFORMATION: Primer Sequence

<400> SEQUENCE: 44

```
Ala Gly Thr Ala Cys Gly Gly Thr Cys Ala Gly Cys Cys Ala Cys Thr
1               5                   10                  15

Cys Gly Ala Cys
            20
```

<210> SEQ ID NO 45
<211> LENGTH: 19
<212> TYPE: PRT
<213> ORGANISM: Artificial Sequence
<220> FEATURE:
<223> OTHER INFORMATION: Primer Sequence

<400> SEQUENCE: 45

```
Ala Gly Gly Thr Cys Cys Gly Ala Thr Cys Thr Ala Cys Cys Ala
1               5                   10                  15

Gly Cys Ala

<210> SEQ ID NO 46
<211> LENGTH: 20
<212> TYPE: PRT
<213> ORGANISM: Artificial Sequence
<220> FEATURE:
<223> OTHER INFORMATION: Primer Sequence

<400> SEQUENCE: 46

Gly Thr Ala Gly Gly Cys Cys Thr Thr Gly Thr Thr Gly Ala Cys Gly
1               5                   10                  15

Gly Thr Gly Thr
            20
```

CRYPTIC METABOLITES AND METHOD FOR ACTIVATING SILENT BIOSYNTHETIC GENE CLUSTERS IN ACTINOMYCETE BACTERIA

CROSS-REFERENCE TO RELATED APPLICATIONS

This application claims the benefit of U.S. Provisional Application No. 62/504,603, filed May 11, 2017, which is hereby incorporated in its entirety by reference.

STATEMENT REGARDING FEDERALLY SPONSORED RESEARCH OR DEVELOPMENT

This invention was made with government support under Grant No. AI124786 awarded by the National Institutes of Health. The government has certain rights in the invention.

FIELD OF THE INVENTION

The present invention relates to cryptic metabolites, and specifically to compositions of matter and a method for activating silent gene clusters in actinomycete bacteria.

BACKGROUND OF THE INVENTION

Bacterial secondary metabolites have been an important source of pharmaceutical compounds and account for some of our most essential medicines. Among bacteria that are recognized as proven producers, actinomycetes, notably *Streptomyces* spp., are the most prolific. They have been responsible for ~50% of clinical antibiotics, as well as numerous anticancer agents. A more recent realization regarding their potential for secondary metabolite production has come from whole genome sequencing. These data have shown that the molecules discovered thus far merely represent the tip of the iceberg, and that most secondary metabolite biosynthetic pathways are not active under normal laboratory growth conditions. Thus, not only are the molecules themselves desirable, but methods that stimulate such pathways could profoundly impact natural products research, and thereby, drug discovery.

Secondary metabolites are generated by dedicated biosynthetic gene clusters (BGCs), sets of usually contiguous genes, whose protein products assemble complex molecules from simple precursors. The BGCs that do not give rise to appreciable concentrations of a metabolite during standard laboratory growth have been described as 'silent' or 'cryptic'. While several approaches have been developed for finding the products of silent BGCs, they do not inform on when, why, and how a producing host activates a given silent BGC; that is, the existing methods are focused on identifying the product(s) of a BGC rather than uncovering the endogenous regulatory circuits that control cryptic metabolism. As such, exogenous signals or cues that elicit cryptic metabolites using the host's regulatory pathways remain largely unknown.

Because *Streptomyces* spp. are an abundant source of silent BGCs and have a proven track record for generating pharmaceutically active compounds, application of a high-throughput elicitor screens (HiTES) to this genera would be especially beneficial. However, difficulties associated with genetic manipulations in *Streptomycetes* spp. make rapid exploration of the regulatory pathways a challenging endeavor. Thus, a method for screening *Streptomycetes* spp. is desirable.

BRIEF SUMMARY OF THE INVENTION

In a first aspect, the present invention is directed to a molecule having the formula:

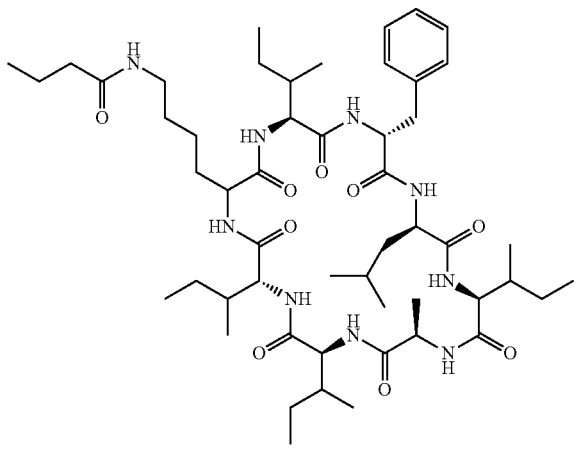 [SMILES: CCCC(=O)NCCCCC1NC(=O)[C@@H](C(C)CC)NC(=O)[C@H](C(C)CC)NC(=O)[C@@H](C)NC(=O)[C@H](C(C)CC)NC(=O)[C@@H](CC(C)C)NC(=O)[C@@H](Cc2ccccc2)NC(=O)[C@H](C(C)CC)NC1=O]

or a pharmaceutically acceptable salt thereof.

In a second aspect, the present invention is directed to a molecule having the structure:

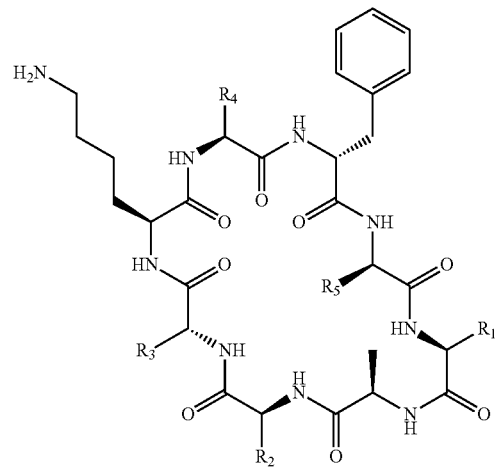

or a pharmaceutically acceptable salt thereof, where $R_1$ and $R_2$ are L-Val, $R_3$ is D-Ile or D-Val, $R_4$ is L-Ile or L-Val, and $R_5$ is D-Leu or D-Val.

In a third aspect, the present invention is directed to a molecule having the structure:

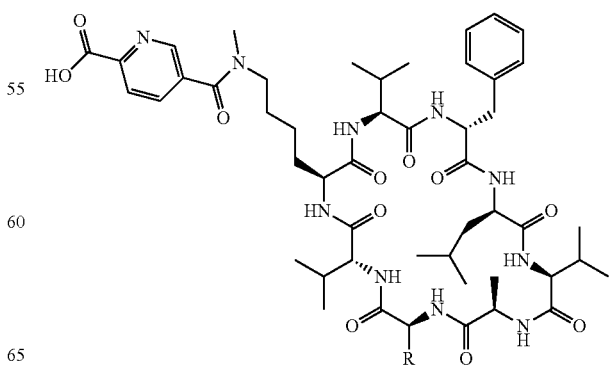

or a pharmaceutically acceptable salt thereof, where R is D-Val or D-Ile.

In a fourth aspect, the present invention is directed to a molecule having the structure:

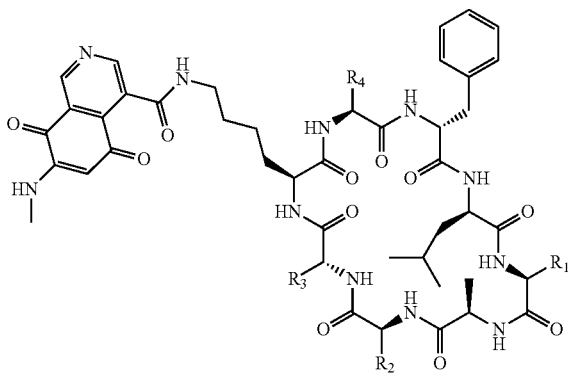

or a pharmaceutically acceptable salt thereof, where $R_1$ and $R_2$ are L-Ile or L-Val, $R_3$ is D-Ile or D-Val, and $R_4$ is L-Ile or L-Val.

In a fifth aspect, the present invention is directed to a molecule having the structure:

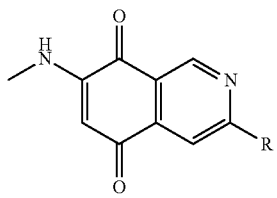

or a pharmaceutically acceptable salt thereof, where R is $CH_2OH$.

In a sixth aspect, the present invention is directed to a molecule having the structure:

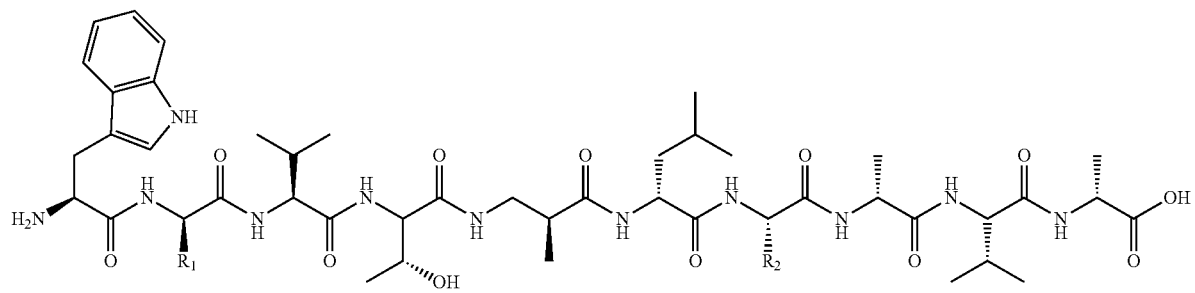

or a pharmaceutically acceptable salt thereof, where $R_1$ and $R_2$ are D-Val and L-Val, respectively, D-Leu and L-Leu, respectively, or D-Leu and L-Ile, respectively.

In a seventh aspect, the present invention is directed to a method for activating silent biosynthetic gene clusters in actinomycete bacteria. The method generally includes providing at least one actinomycete bacterial cell having at least one gene cluster that is silent or lowly-expressed and at least one of a promoter from a targeted gene cluster fused to at least one reporter gene at a neutral site or the promoter fused to at least one reporter gene at a site within the targeted gene cluster. The bacterial cell is then exposed to test compounds from a small molecule library, the expression of the at least one reporter gene is measured at a first and second point in time, and identifying activation of gene clusters by comparing the difference between the measurements at the two points in time to a threshold.

Advantageously, the actinomycete bacteria is from the genus *Streptomyces*. Further, the at least one reporter gene may be eGFP, and may also include at least three copies of eGFP.

It is also advantageous when the neutral site is attB, or the site within a targeted gene cluster.

Certain embodiments may utilize a positive and negative control. Further, the threshold amount may be a 2.5 fold induction of the reporter gene, or more.

It may be advantageous when a second actinomycete bacterial cell is utilized that is a different strain than the strain of the at least one actinomycete bacterial cell. It may also be advantageous when a second actinomycete bacterial cell is utilized along with any silent biosynthetic gene cluster in that actinomycete.

BRIEF DESCRIPTION OF THE DRAWINGS

FIG. 1 is a flowchart of a disclosed method.

FIG. 8 is a table of data from a series of bioassays.

DETAILED DESCRIPTION OF THE INVENTION

As used herein, articles such as "a" and "an" when used in a claim, are understood to mean one or more of what is claimed or described.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the term "at least one" means one or more and thus includes individual components as well as mixtures/combinations.

As used herein, the terms "include", "includes" and "including" are meant to be non-limiting.

The present invention is directed to a method for activating silent biosynthetic gene clusters in actinomycete bacteria, and several compositions of matter resulting therefrom.

Referring now to FIG. 1, a method (10) for activating silent biosynthetic gene clusters in actinomycete bacteria is disclosed. While this method applies to any actinomycete bacteria, in certain embodiments, the actinomycete bacteria is from the genus *Streptomyces* or *Saccharopolyspora*. In certain embodiments, the bacteria is *Streptomyces albus*, *Streptomyces coelicolor*, *Saccharopolyspora erythraea*, *Streptomyces avermitilis*, or a variant thereof.

The method generally begins by providing (20) at least one actinomycete bacterial cell that contains at least one gene cluster that is silent or lowly-expressed. Further, the bacterial cell also contains at least one of either (i) a promoter from a targeted gene cluster fused to at least one reporter gene at a neutral site, or (ii) the promoter fused to at least one reporter gene at a site within the targeted gene cluster.

The method is not limited to a single actinomycete bacterial cell; certain embodiments may also comprise an additional actinomycete bacterial cell that is a different strain than the strain of the at least one actinomycete bacterial cell. Additionally, the method may also utilize the additional actinomycete bacterial cell and any silent biosynthetic gene cluster in that additional actinomycete.

While any reporter gene may be utilized, certain embodiments utilize eGFP or a derivative thereof. In certain embodiments, two or more reporter genes (including copies of the same reporter gene) are preferred, and three or more reporter genes are more preferable.

Figure 2A:
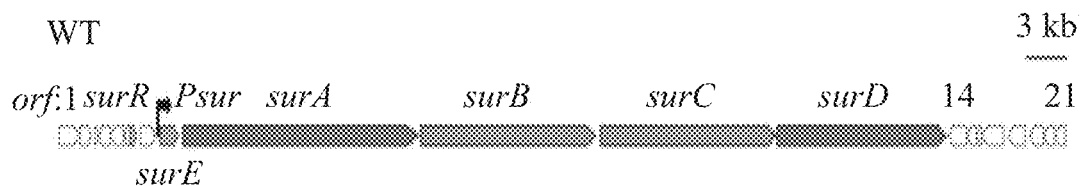
FIG. 2A is a depiction of the sur cluster of a wild-type *S. albus*, where surA-surD encode non-ribosomal peptide synthetases, surE a β-lactamase, and surR a GntR-type transcriptional regulator, and where the black arrow represents the promoter.
Figure 2B:
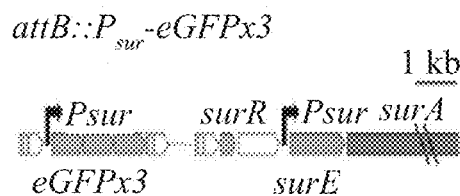
FIGS. 2B and 2C are depictions of embodiments of a genetic construct.

One example of the first step of the method can be seen in reference to FIGS. 2A-2B. In one embodiment, *S. albus* J1074 (hereafter *S. albus*) was selected as the target organism, because it is genetically tractable and serves as a commonly-used heterologous host for expression of actinomycete genes and gene clusters. Along with *Streptomyces coelicolor* M145, *S. albus* serves as a model strain for this genus. Moreover, like other *Streptomycetes*, *S. albus* harbors an excess of silent BGCs. Among these, a large non-ribosomal peptide synthetase (NRPS) gene cluster was chosen, to which a compound has not yet been associated (See FIG. 2A and Table 1, below). Recent results by the Matsunaga group suggest it is homologous to a cluster in a marine *Streptomyces* strain, and that it gives rise to the so-called surugamides, consistent with the MS-based results by Mohimani et al. Hereinafter, this cluster is named sur, based on previous results and those reported herein.

TABLE 1

Annotation of the surugamide biosynthetic gene duster (sur).

| Orf Name | Gene locus ID | Length (AA) | Homology-Based Predicted Function |
|---|---|---|---|
| orf1 | XNR3458 | 475 | Sulfoacetaldehyde dehydrogenase |
| orf2 | XNR3457 | 269 | Pimeloyl-ACP methyl ester carboxyesterase |
| orf3 | XNR3456 | 85 | MbtH protein |
| orf4 | XNR3455 | 265 | ABC transport system, membrane protein |
| orf5 | XNR3454 | 313 | ABC transporter, ATP-binding protein |
| orf6 | XNR3453 | 123 | Hypothetical protein |
| SurR | XNR3452 | 138 | GntR family DNA-binding transcriptional regulator |
| orf7 | XNR3451 | 365 | Putative membrane protein |
| SurE | XNR3450 | 451 | Beta-lactamase |
| SurA | XNR3449 | 5733 | NRPS (A-C-A-E-C-A-C-A-E-C-A) |
| SurB | XNR3448 | 4265 | NRPS (A-C-A-E-C-A-C-A) |
| SurC | XNR3447 | 7691 | NRPS (C-A-C-A-E-C-A-C-A-E-C-A-C-A-E) |
| SurD | XNR3446 | 4114 | NRPS (C-A-C-A-E-C-A-E) |
| orf8 | XNR3445 | 448 | Drug resistance transporter, EmrB/QacA subfamily |
| orf9 | XNR3444 | 203 | TetR family transcriptional regulator |

TABLE 1-continued

Annotation of the surugamide biosynthetic gene cluster (sur).

| Orf Name | Gene locus ID | Length (AA) | Homology-Based Predicted Function |
| --- | --- | --- | --- |
| orf10 | XNR3443 | 102 | Hypothetical protein |
| orf11 | XNR3442 | 524 | EmrB/QacA subfamily drug resistance transporter |
| orf12 | XNR3441 | 406 | Secreted protein |
| orf13 | XNR3440 | 329 | Osmoprotectant transport system, substrate-binding protein |
| orf14 | XNR3439 | 253 | Osmoprotectant transport system, permease protein |
| orf15 | XNR3438 | 236 | Osmoprotectant transport system, permease protein |

Bioinformatic analysis of the sur cluster identified only one promoter sequence stir, upstream of surE (P FIG. 2A). To apply HiTES using this promoter, two reporter systems, XylE and eGFP were considered, both of which have previously been employed in S. coelicolor. The frequently-used lacZ reporter gene is not applicable to Streptomycetes as many members encode endogenous β-galactosidase activities. Two constructs for each reporter gene were constructed, one, in which xylE or eGFP was driven by $P_{sur}$ ($P_{sur}$-eGFP and $P_{sur}$-xylE) and a second as a positive control, where each reporter gene was driven by the constitutively active erythromycin resistance gene promoter, $P_{ermE}$ ($P_{ermE}$ eGFP and $P_{ermE}$-xylE, Tables 2-3). Both constructs were inserted into an attB neutral site in the S. albus chromosome and examined using the catechol assay (XylE) or fluorescence (eGFP). Rapid and reliable results proved difficult with attB::$P_{ermE}$-xylE. By contrast, attB::$P_{ermE}$-eGFP gave reproducible, albeit weak, signal.

Figure 2C:
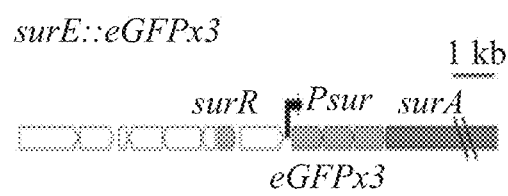
Figure 2D:
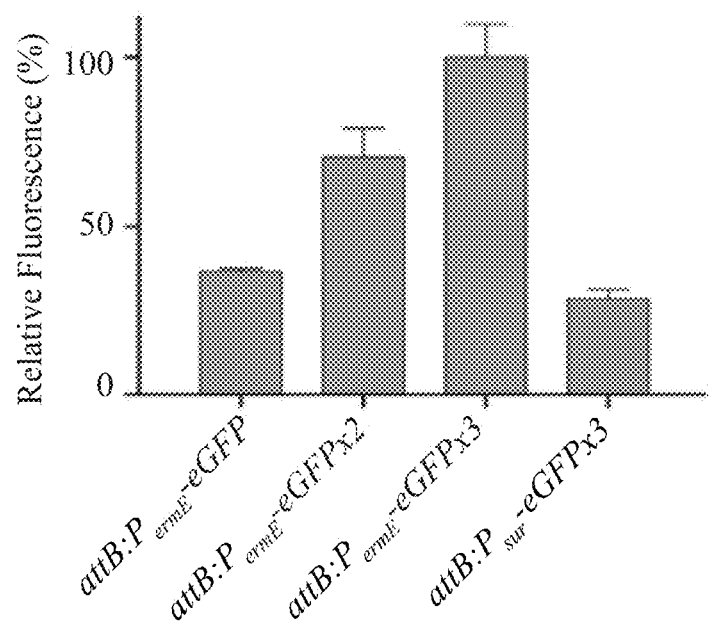
FIG. 2D is a graph of reporter assays measuring signal amplification with one, two, or three copies of eGFP driven by $P_{ermE}$.

The advantage of reporter genes such as xylE and lacZ, in comparison to eGFP, is that the signal is amplified by enzymatic activity. On the other hand, a benefit of eGFP is that addition of substrate or cell lysis is not required prior to readout. To achieve signal amplification with eGFP, two additional genetic constructs were constructed, one containing two and another containing three copies of eGFP ($P_{ermE}$-eGFPx2 and $P_{ermE}$-eGFPx3). AttP-mediated neutral site insertion, followed by fluorescence assays resulted in significantly increased signal and a good Z' score of 0.51 with attB::$P_{ermE}$-eGFPx3 (See FIGS. 2B-2D), which is sufficient for reliable results in a high-throughput assay format.

Two different S. albus reporter strains were created for activating the sur cluster: attB::$P_{sur}$-eGFPx3, where the reporter is inserted at an attB neutral site (see FIG. 2B), as described above, as well as surE::eGFPx3 (see FIG. 2C), in which the reporter genes replace surE and are therefore directly downstream of $P_{sur}$ (FIGS. 2B-2C, Table 1). The latter construct was generated to avoid possible polar effects that can arise from regulatory elements that may be adjacent to a given attB site.

Referring back to FIG. 1, the disclosed method typically includes 4 more steps: (i) exposing (30) the bacterial cell to test compounds from a small molecule library, (ii) measuring (40) the expression of the at least one reporter gene at a first point in time, (iii) measuring (50) the expression of the at least one reporter gene at a second point in time, and (iv) identifying (60) activation of gene clusters by determining whether the expression of the at least one reporter gene has increased by more threshold amount from the first point in time to the second point in time.

These next four steps are seen be referring to the previously described example. In the previously described example, HiTES was carried out using the two constructs seen in FIGS. 2B and 2C with a ~500-member natural products library. Each S. albus construct was grown in a 96-well format, supplemented with the compound library, and the effect of each compound on the silent BGC determined using eGFP-derived fluorescence. Interference from naturally fluorescent compounds in the library was eliminated by subtracting the fluorescence reads at 60 hours from those collected at t=0, immediately after addition of the library members.

Figure 3A:
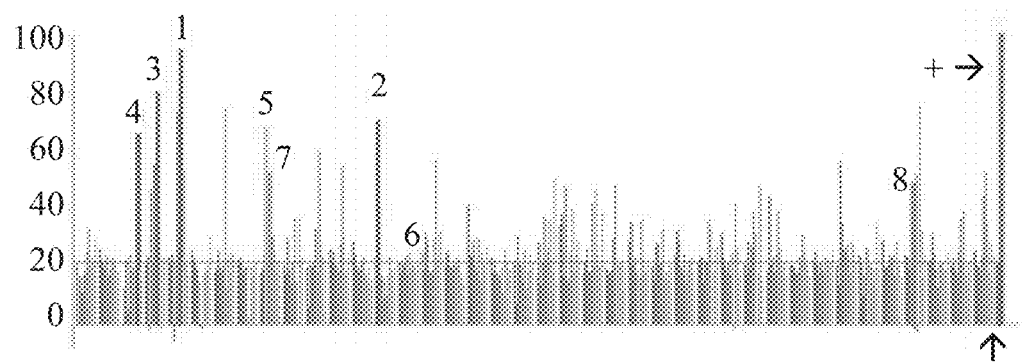
FIGS. 3A and 3B are graphs of a high-throughput elicitor screen to induce the sur cluster.
Figure 3B:
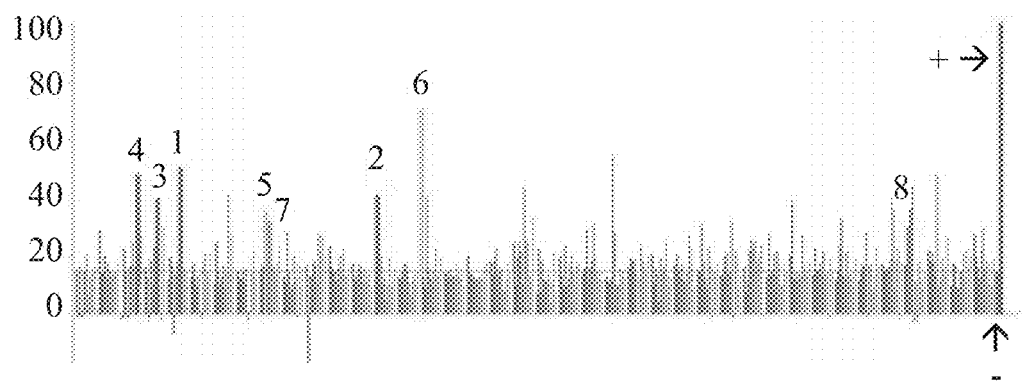

Referring to FIGS. 3A and 3B, results for both genetic constructs are shown. These graphs show relative expression of a neutral site reporter, attB::$P_{sur}$-eGFPx3 (FIG. 3A) or targeted sur reporter, surE::eGFPx3 (FIG. 3B) as a function of exogenously-supplied small molecules. Each bar represents the level of expression of sur in the presence of a single candidate elicitor. Plus signs denote the positive control, attB::$P_{ermE}$-eGFPx3. Minus signs denote the negative controls, attB::$P_{sur}$-eGFPx3 (3A) or surE::eGFPx3 (3B) in the absence of any metabolites. The expression has been normalized to the positive control.

In this example, the threshold amount was a 2.5 fold induction of eGFP-derived fluorescence emission. Thus, hits were considered those that gave at least a 2.5-fold induction of eGFP-derived fluorescence emission. However, in other embodiments, hits may be those giving at least a 2 fold induction, more preferably at least a 3 fold induction, and more preferably at least a 4 fold induction.

Figure 3C:
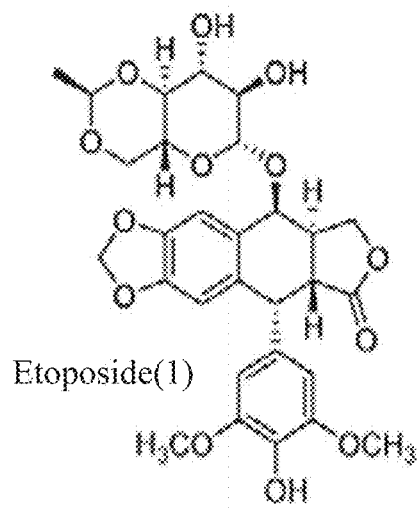
FIGS. 3C-3H are structures of the top six elicitors in one embodiments.
Figure 3E:
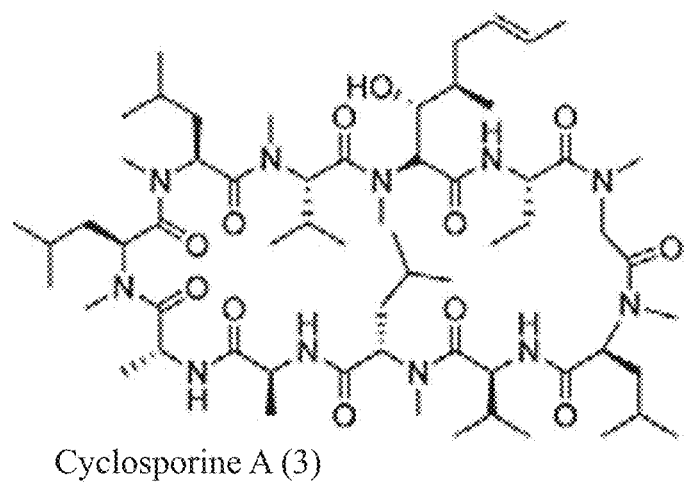
Figure 3G:
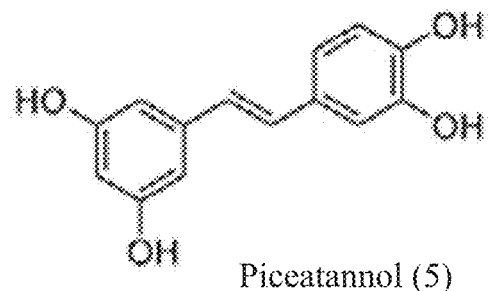
Figure 3D:
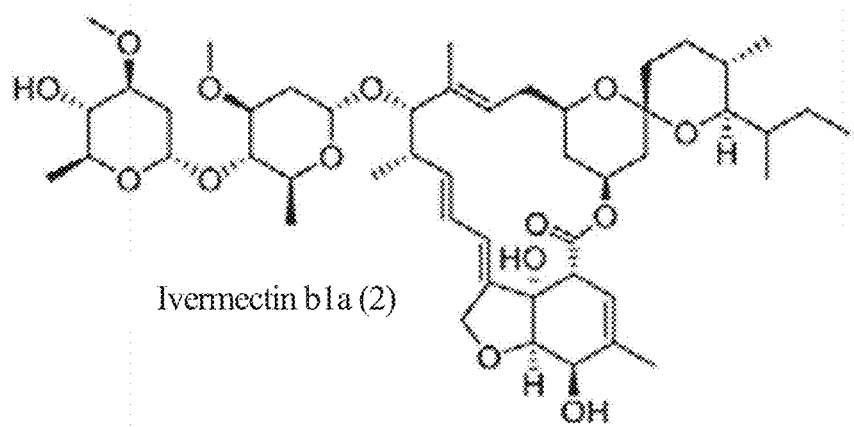
Figure 3F:
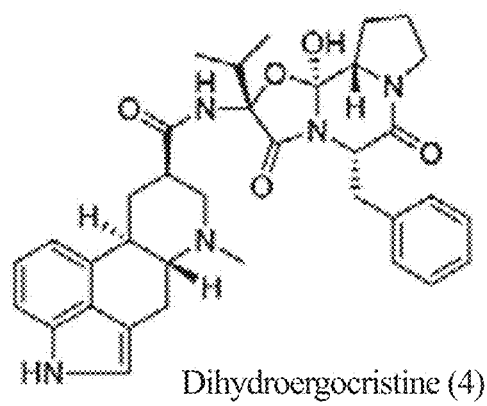
Figure 3H:
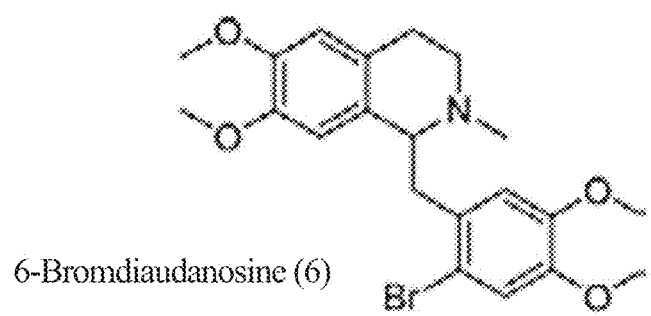

The results from the two reporter strains were largely congruous though some differences can be observed (FIGS. 3A-3B). For example, some hits were only observed in attB::$P_{sur}$-eGFPx3, but not in surE::eGFPx3, possibly because of the aforementioned polar effects associated with attB sites. In both cases, up to 5-fold induction of sur expression could be identified. Comparison of the two assays and identification of molecules that induced the sur cluster in both reporter strains provided the following best hits: the natural product-derived anticancer agent etoposide (1, FIG. 3C), the famous anti-parasitic agent and Streptomyces avermitilis-derived ivermectin (2, FIG. 3D), the immunosuppressant cyclosporine A (3, FIG. 3E), the nootropic dihydroergocristine (4, FIG. 3F), plant-derived piceattanol (5, FIG. 3G), and bromolaudanosine (6, FIG. 3H). These results indicate that sur expression is subject to the presence and nature of exogenous small molecules in the media.

Figure 4A:
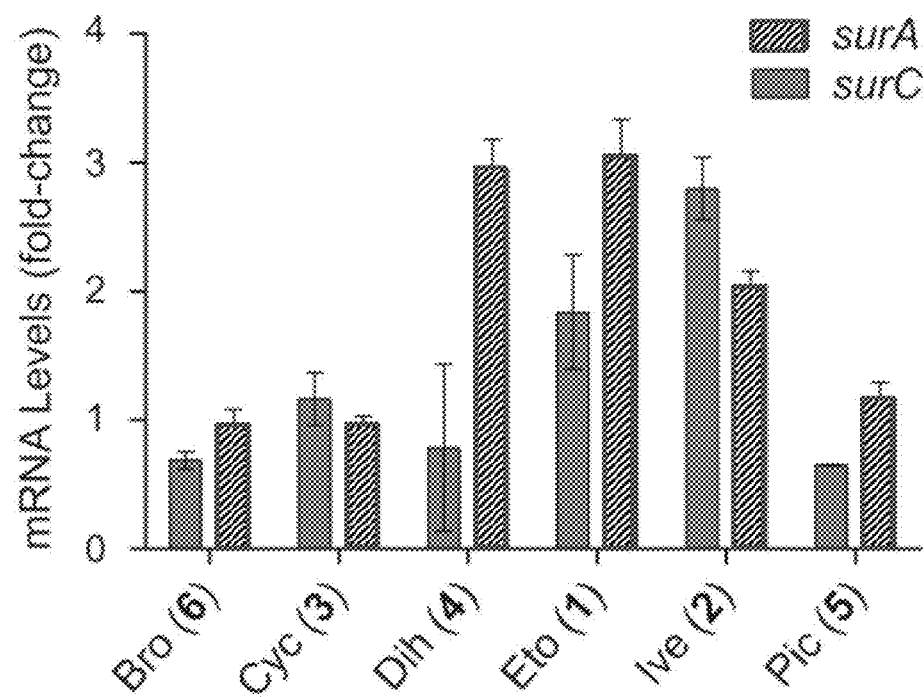
FIG. 4A is a graph of an RT-qPCR analysis of the seleted elicitors on sur expression, depicting the observed fold-change in surA and surC mRNA levels compared to a DMSO negative control.
Figure 4B:
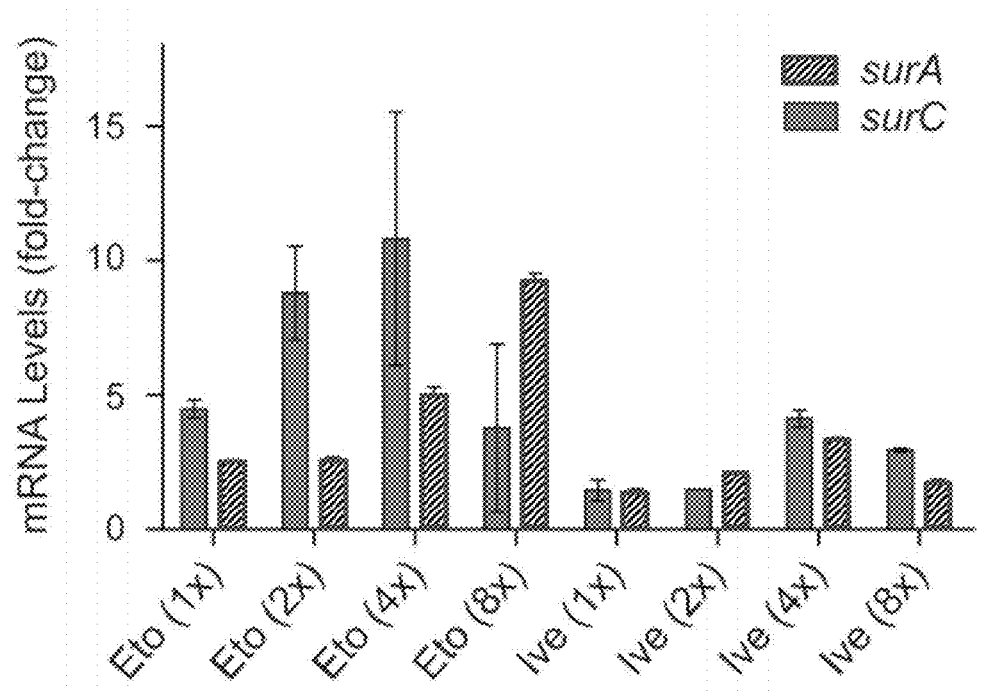
FIG. 4B is a graph of the concentration-dependence of the induction of sur by two selected elicitors, determined by RT-qPCR, depicting the observed fold-change in mRNA levels with respect to a DMSO negative control.

In the example above, the effects of these putative elicitors on the sur cluster were validated by performing a RT-qPCR with wt S. albus. Upon exposure of S. albus to each elicitor or DMSO (control), total RNA was be isolated, converted to cDNA and the surA and surC transcripts quantified by qPCR. The results show a 3-fold induction of surA and surC by ivermectin, etoposide, and dihydroergocristine, consistent with the HiTES results (FIG. 4A). More modest effects were observed with the other three elicitors. We thus focused our efforts on the top two elicitors, etoposide (1, FIG. 3C) and ivermectin (2, FIG. 3D). To further verify the effect of 1 and 2, a dose-response assay was carried out. With both elicitors, a concentration-dependent induction of sur was observed, yielding optimal upregulation at a final concentration of ~23 μM (etoposide) and ~30 μM (ivermectin) (FIG. 4B). These concentrations induced a ~10-fold (etoposide) and 4.5-fold (ivermectin) upregulation of surC. Etoposide had anti-bacterial effects on *S. albus* and the diminished response observed at high concentrations correlated with antibiosis. Thus, as reported with trimethoprim and other antibiotics, etoposide exhibits hormetic effects, stimulating metabolism at sub-inhibitory concentrations, while killing *S. albus* at higher concentrations.

Figure 5:
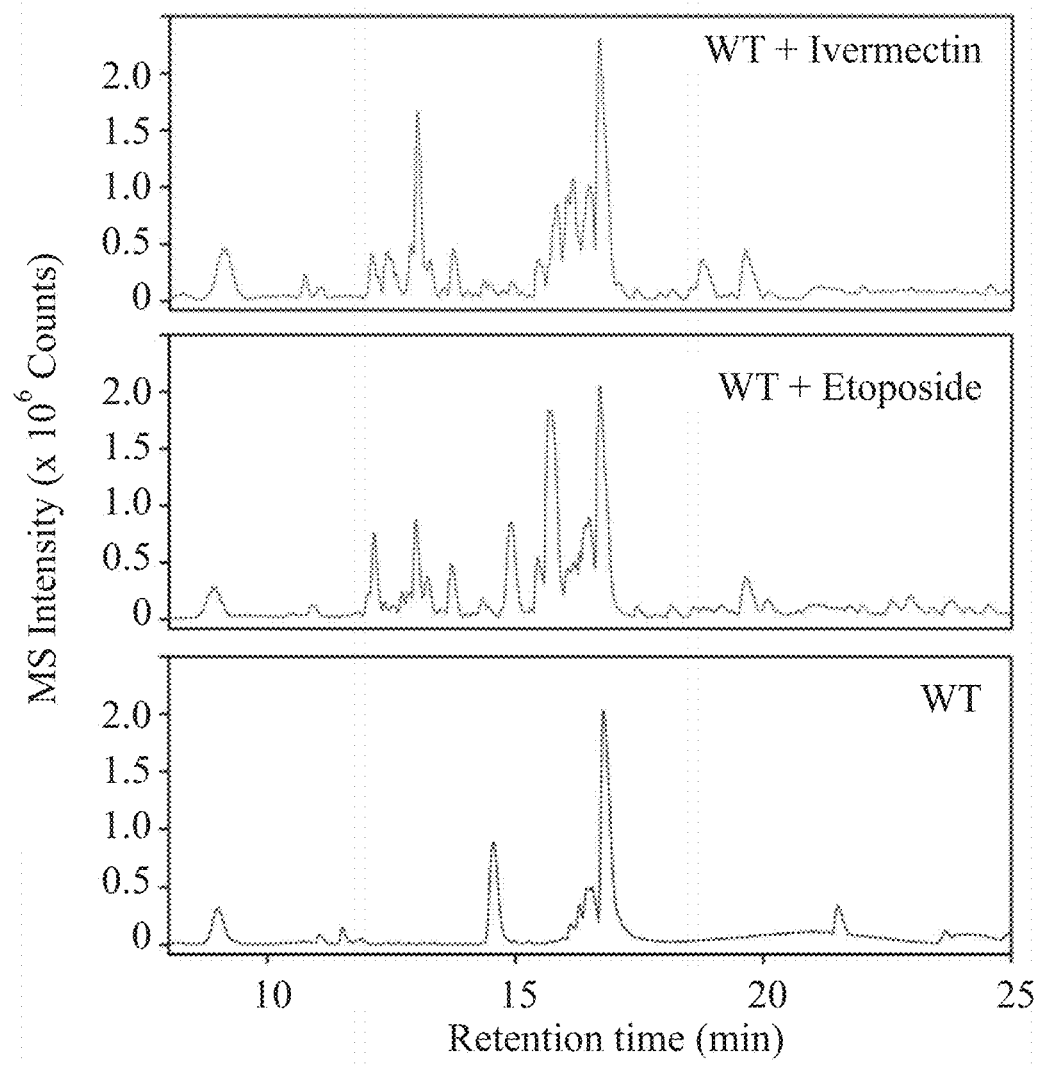
FIG. 5 is a base-peak chromatogram HPLC-MS analysis of the secondary metabolome of *S. albus* in response to ivermectin (top), Etoposide (middle) and DMSO negative control (bottom).

Finally, effect of both inducers on the *S. albus* secondary metabolome were examined. *S. albus* was treated with each elicitor, cultured for 4 days, and the cell-free supernatants analyzed by HPLC-Qtof-MS. The results show a remarkable induction of a large array of secondary metabolites by etoposide and ivermectin (FIG. 5). Despite their disparate structures, 1 and 2 stimulated production of very similar metabolomes, with many of the same peaks observed in both cultures.

To facilitate the identification of cryptic metabolites of the sur cluster, two insertional gene inactivation mutants were generated, surA::apr (LlsurA) and surB::apr (LlsurB) where the surA or surB genes were replaced by the apramycin resistance marker (apr). Comparison of the supernatants of wt *S. albus* with the two mutants, in the presence of ivermectin, allowed identification of compounds generated by sur. High-resolution (HR) MS analysis indicated that these compounds fall into five categories, suggesting that sur has a diverse output: four of these were dependent on the presence of surA, while one required the presence of surB.

Within each of the five groups, the most abundant members were isolated and solved their structures by HR-MS, HR tandem-MS, and 1D/2D NMR (See, e.g., FIGS. 6A-6F).

The first group (see FIG. 6A) consisted of compounds with m/z 912, 898, 884, 870, 856, and 842 and lacked any characteristic UV-visible absorption features. NMR data showed that the first two were identical to the octapeptides surugamide A (9) and D (10), which were previously reported by Takada et al from a marine Streptomycete. The other four analogs, however, were new metabolites. These were called surugamide G, H, I, and J (11-14). Referencing FIG. 6A, the structure of the six compounds is described in Table 4, below.

TABLE 4

|  | R1 | R2 | R3 | R4 | R5 |
|---|---|---|---|---|---|
| surugamide A (9) | L-Ile | L-Ile | D-Ile | L-Ile | D-Leu |
| surugamide D (10) | L-Ile | L-Val | D-Ile | L-Ile | D-Leu |
| surugamide G (11) | L-Val | L-Val | D-Ile | L-Ile | D-Leu |
| surugamide H (12) | L-Val | L-Val | D-Ile | L-Val | D-Leu |

TABLE 4-continued

|  | R1 | R2 | R3 | R4 | R5 |
|---|---|---|---|---|---|
| surugamide I (13) | L-Val | L-Val | D-Val | L-Val | D-Leu |
| surugamide J (14) | L-Val | L-Val | D-Val | L-Val | D-Val |

Their production was vastly increased in the presence of ivermectin and etoposide (FIG. 4B). Complete structural assignment by NMR showed they consist of the same 8mer cyclic scaffold as surugamide A with variations in the amino acid sequence (FIGS. 5A, S5-S9, and Tables S5-S6). The stereo-chemistry was assigned based on an analysis of the bio-synthetic gene cluster using bioinformatic methods. It is identical to that of surugamide A, which was determined experimentally.

Thus, an embodiment of a disclosed composition of matter identified from the use of this method may comprise a molecule having the structure:

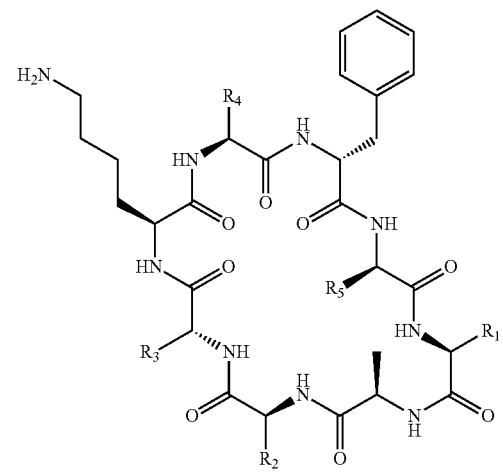

or a pharmaceutically acceptable salt thereof, where $R_1$ and $R_2$ are L-Val, $R_3$ is D-Ile or D-Val, $R_4$ is L-Ile or L-Val, and $R_5$ is D-Leu or D-Val.

Figure 6A:
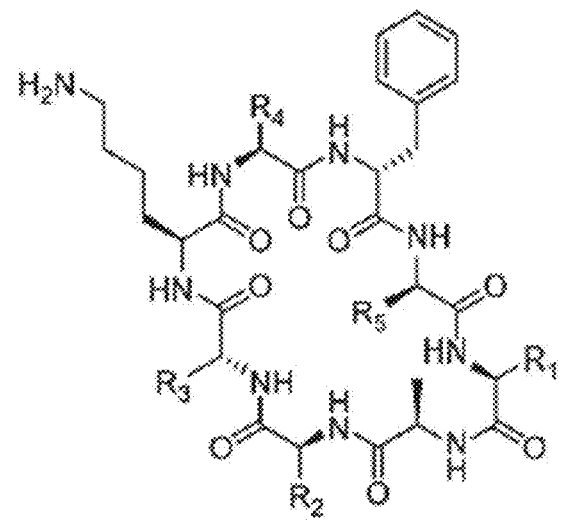
FIGS. 6A-F are the small molecule products of the sur cluster induced by etoposide and ivermectin.
Figure 6B:
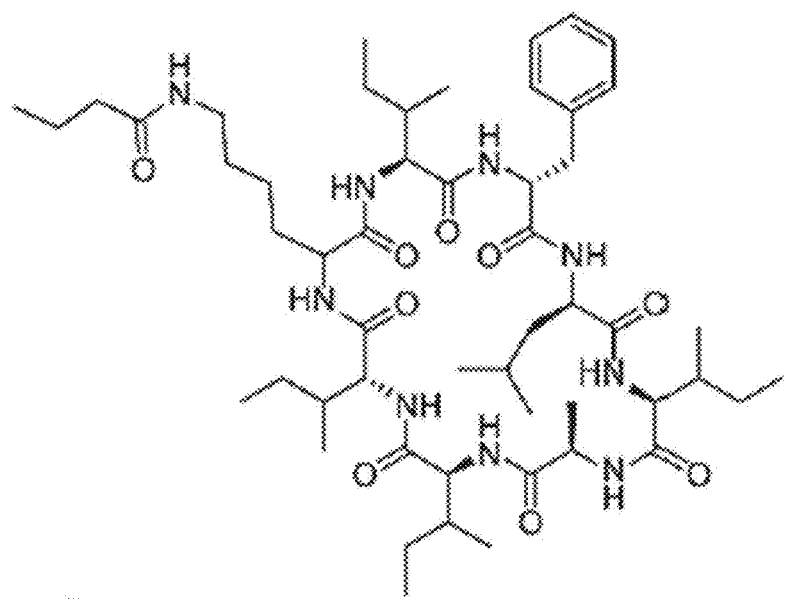
Figure 6C:
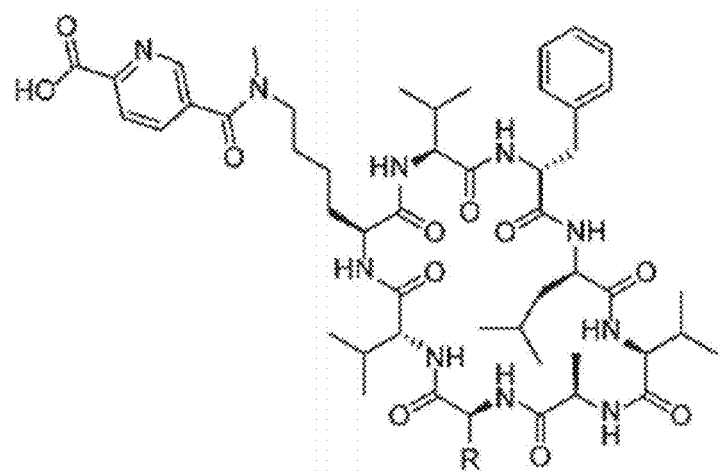
Figure 6D:
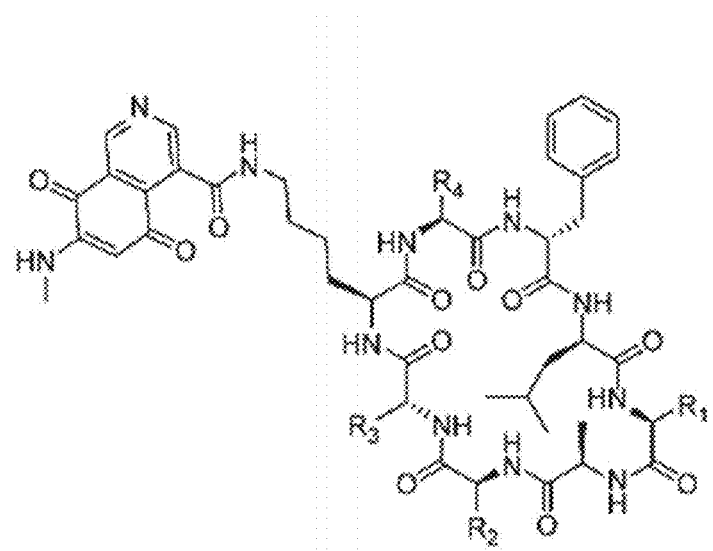
Figure 6E:
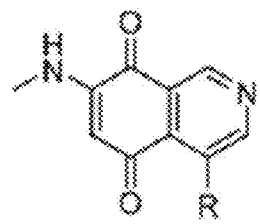
Figure 6F:
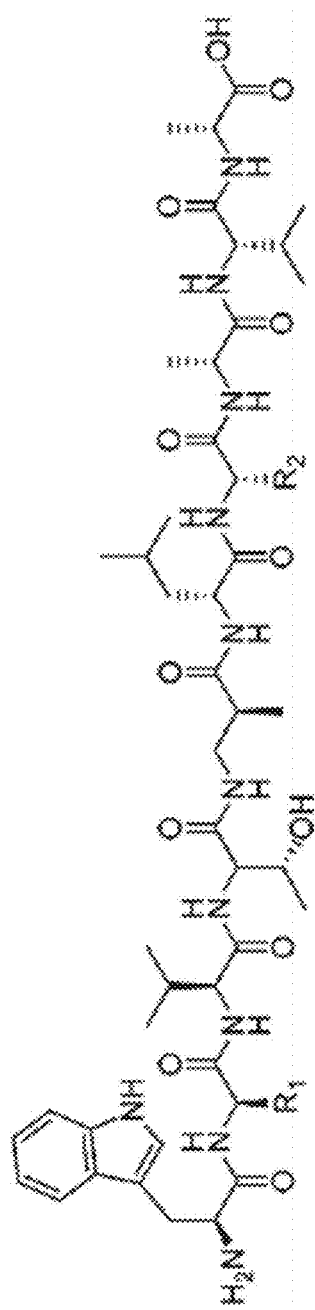

The second group of metabolites, whose production was only observed in the presence of ivermectin/etoposide and abolished in the LlsurA mutant, consisted of m/z 982, 968, 954, 940, and 926 (FIG. S3, Table S4). All variants are new metabolites as determined by HR-MS analysis and comparison to a database of known products. These are called acyl-surugamides A E. The structure of variant A was determined by NMR. $^1$H and COSY data showed that it consists of two spin systems, an octapeptide scaffold as well as a butyryl group. Analysis of TOCSY, HMBC, and NOESY data, which showed correlations between the butyryl $^1$Hs and the lysine side-chain $^1$Hs, clearly pointed to acylation of the lysine side-chain amine of surugamide and thus completed the structural assignment (FIG. 6B). This subgroup of metabolites is a novel, side-chain-modified variant of surugamides and indicates that additional tailoring of the octapeptide scaffold further amplifies the output of the sur cluster in the presence of elicitors.

Thus, an embodiment of a disclosed composition of matter identified from the use of this method may comprise a molecule having the structure:

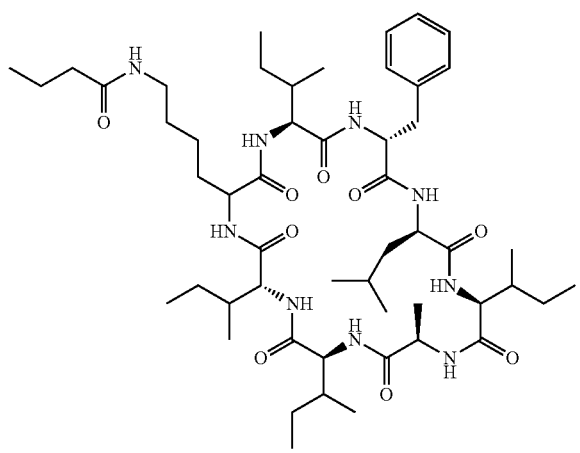 [SMILES: CCCC(=O)NCCCCC1NC(=O)[C@@H](C(C)CC)NC(=O)[C@H](C(C)CC)NC(=O)[C@@H](C)NC(=O)[C@H](C(C)CC)NC(=O)[C@@H](CC(C)C)NC(=O)[C@@H](Cc2ccccc2)NC(=O)[C@H](C(C)CC)NC1=O]

or a pharmaceutically acceptable salt thereof. In certain other embodiments, the butyryl group may be replaced by any other length of acyl chain, including those containing substituents such as hydroxyl or halide groups.

A third group of compounds elicited by ivermectin/etoposide, with m/z of 1019 and 1033 (pyrisurugamides A and B, FIG. 6C), were also dependent on surA, but not surB. Structural analysis of variant A by 1D/2D NMR revealed two spin systems, one consisting of the surugamide scaffold and the second bearing only aromatic $^1$Hs. Analysis of HSQC and HMBC spectra unveiled this second spin system as an unusual moiety, a pyridine-2,5-dicarboxylic acid (PDA), condensed with the lysine side-chain amine of surugamide. A methyl group with $8_H$ and $8_C$ of 2.67 and 38.2, respectively, correlated with the pyridine moiety and was assigned as an amide-methyl substituent, thus completing the structural assignment (16-17). Pyrisurugamide A (16) and B follow the FIG. 6C structure, where R is D-Val for surugamide A, and R is D-Ile for Pyrisurugamide B. Pyrisurugamides are novel metabolites and their presence suggests that PDA is generated in S. albus along with enzyme(s) that can condense it with the lysine amine of surugamides. Its chemical synthesis and biological evaluation have revealed it as a potent antiviral compound and as inhibitor of various enzymes, notably prolyl-4-hydroxylase. Pyrisurugamides represent a combination of two bioactive fragments that are joined to generate new hybrid molecules. In addition to acylation by a butyryl group, the lysine amine of surugamide provides an anchor for further modifications.

Thus, an embodiment of a disclosed composition of matter identified from the use of this method may comprise a molecule having the structure:

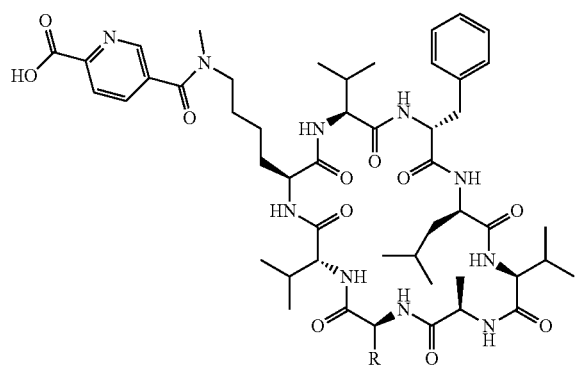

or a pharmaceutically acceptable salt thereof, where R is D-Val or D-Ile.

Another group of compounds significantly larger than those discussed above (m/z 1126, 2×1112, 2×1084, and 1070) were identified. These again consisted of two spin systems, one of which was the surugamide scaffold. The lysine residue in the surugamide portion was again found to be acylated, in this case with an unusual second spin system with a small $^1$H/$^{13}$C ratio, as shown by HMBC, NOESY, and HR-MS data. Further, the UV-vis spectrum of this set of compounds exhibited features typical of quinones, consisting of a broad absorption band with an $A_{max}$ of 470 nm. Analysis of a full set of 1D/2D NMR data ultimately showed that the second spin system consists of a novel isoquinoline quinone moiety. These metabolites were called albucyclones A-F (18-23, FIGS. 6D, 4D). Within this family, structures were assigned to all six variants. They all contain the unusual isoquinoline quinone acyl group, but vary in the sequence of the octapeptide. Referencing FIG. 6D, the structure of the six compounds is described in Table 5, below.

TABLE 5

|  | R1 | R2 | R3 | R4 |
| --- | --- | --- | --- | --- |
| albucyclone A (18) | L-Ile | L-Ile | D-Ile | L-Ile |
| albucyclone B (19) | L-Ile | L-Val | D-Ile | L-Ile |
| albucyclone C (20) | L-Val | L-Ile | D-Ile | L-Ile |
| albucyclone D (21) | L-Val | L-Val | D-Ile | L-Val |
| albucyclone E (22) | L-Val | L-Ile | D-Val | L-Val |
| albucyclone F (23) | L-Val | L-Val | D-Val | L-Val |

Like pyrisurugamides, the albucyclones are a novel combination of two natural products that likely arises from cross-talk between two different BGCs. The induction of albucyclones further emphasizes that under stimulatory conditions, the output of the sur cluster can be vastly amplified to generate new, hybrid molecules.

Thus, an embodiment of a disclosed composition of matter identified from the use of this method may comprise a molecule having the structure:

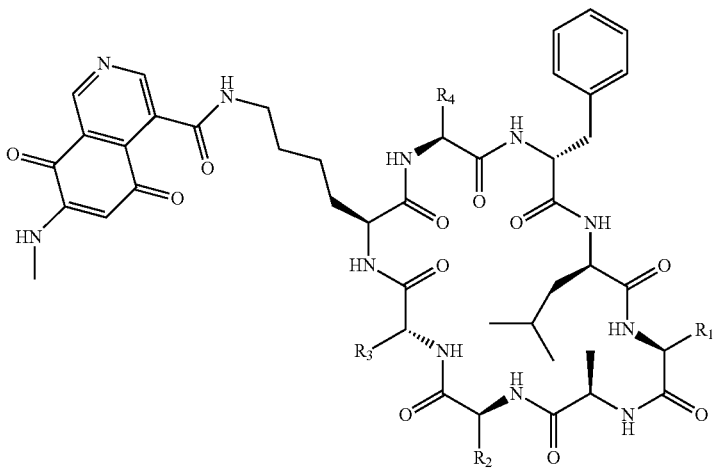

or a pharmaceutically acceptable salt thereof, where $R_1$ and $R_2$ are L-Ile or L-Val, $R_3$ is D-Ile or D-Val, and $R_4$ is L-Ile or L-Val.

A family of low molecular weight compounds were identified that were only induced by ivermectin and displayed the expected quinone UV-vis spectrum. The structures of two compounds with m/z of 219 and 203 were elucidated (FIG. 5E). The former is a novel compound; and was given the trivial name albuquinone A (24). It is similar to the side chain in the albucyclones. The second compound (25, m/z 203, 3-methyl-7-methylamino-5,8-isoquinolinedione) was similar to the mansouramycins, metabolites previously isolated from a marine Streptomycete (FIG. S20). This compound has broad and potent anticancer activity with IC50s ranging from 0.2-50 µM against 36 diverse cancer cell lines, with a mean IC50 of 3.5 µM. Together, these results suggest that ivermectin induces other silent BGCs that generate bioactive metabolites; one these BGCs, in cross-talk with the sur cluster, gives rise to the albucyclones. It is possible that the PDA moiety in pyrisurugamides is a biosynthetic precursor or intermediate of albuquinone A. The structure of albuquinone A can be see in FIG. 6E, where R is $CH_2OH$.

Thus, an embodiment of a disclosed composition of matter identified from the use of this method may comprise a molecule having the structure:

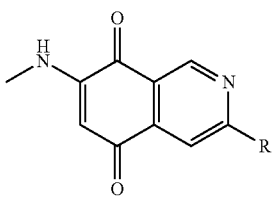

or a pharmaceutically acceptable salt thereof, where R is $CH_2OH$.

The last group of cryptic metabolites produced by the sur cluster consisted of m/z 1056, 1042, and 1070 (Table S4). This was the only set of compounds that was dependent on surB, but not surA. Their structures were investigated by HR tandem-MS, which revealed all b and y ions of a linear decapeptide product. One compound (m/z 1056) was identical to surugamide F, previously reported. The second and third are new analogs, which called surugamide F2 and F3. Like the F variant, they also contain an unusual β-amino acid, but surugamide F2 has a Leu-to-Val substitu-tion at position 2, while surugamide F3 has a Val-to-Leu/Ile substitution at position 7 ( ). Thus, the output of the sur cluster in S. albus is similar to that previously reported from the marine strain Streptomyces sp. JAMM992, in that both produce a decapeptide as well as a cyclic octapeptide. The synthesis of two distinct compounds from the same gene cluster is highly unusual. Our mutagenesis data and bioinformatic analyses suggest that SurA and SurD are responsible for production of the octapeptides (FIG. 2A), while SurB and SurC give rise to the decapeptide (FIG. 2A), analogous to results by Ninomiya et al. Referencing FIG. 6F, the structure of the three compounds is described in Table 6, below.

TABLE 6

|  | R1 | R2 |
|---|---|---|
| surugamide F (26) | D-leu | L-Val |
| surugamide F2 (27) | D-Val | L-Val |
| surugamide F3 (28) | D-Leo | L-Leu/L-Ile |

Thus, an embodiment of a disclosed composition of matter identified from the use of this method may comprise a molecule having the structure:

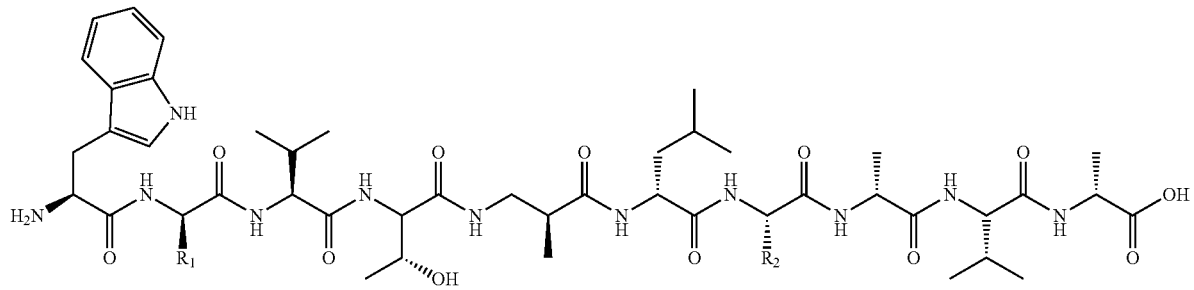

or a pharmaceutically acceptable salt thereof, where $R_1$ and $R_2$ are D-Val and L-Val, respectively, D-Leu and L-Leu, respectively, or D-Leu and L-Ile, respectively.

Each of these groups of compounds may be used prophylactically or non-prophylactically for treatment of a patient, whether human or otherwise. For example, one of the compounds may be used as an antibiotic or as a means to treat or prevent cancer, by providing an appropriate dosage to a subject or target. In some embodiments, the compound may be included in a solution or mixture, and injected or orally administered to a patient.

As alluded to above, Streptomycete secondary metabolites are often adorned with exquisite, sometimes useful, bioactivities. To examine the activities of the cryptic metabolites above, a series of bioassays were carried out (see FIG. 8). Surugamides have been shown to harbor inhibitory activity against cathepsin B, a cysteine protease and anticancer target. Surugamides G-J were investigated in a cathepsin B assay and showed good inhibitory activity, in line with those for surugamide A. Notably, surugamide I was a strong cathepsin B inhibitor with an IC50 of 9.0 µM. Acyl-surugamide A, albucyclones, and albuquinone were also investigated in antibacterial and antifungal assays. While albucyclones and albuquinone did not reveal significant antibiotic activity against the strains tested, acylsurugamide A exhibited strong antifungal activity with an IC50 of 3.5 µM against S. cerevisiae. These results underline the utility of HiTES in uncovering cryptic, bioactive metabolites.

Figure 7A:
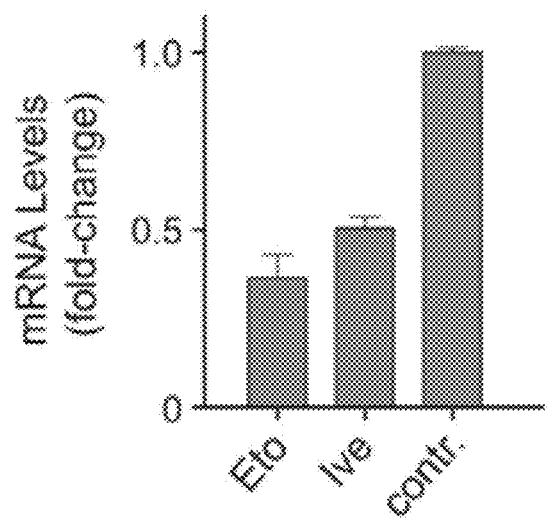
FIG. 7A is a graph of a RT-qPCR analysis of the effect of etoposide and ivermectin on the expression of surR, showing the observed fold-change in surR mRNA levels compared to a DMSO negative control.

Having identified inducers of the cryptic sur cluster and characterized its various products, the mechanism of induction by ivermectin and etoposide was explored using a forward genetic approach. The sur cluster appears to express a pathway-specific transcriptional regulator of the GntR family, which was named SurR (FIG. 2A). One possible mechanism of induction by the elicitors could involve modulation of the expression of surR. To test this hypothesis, the level of expression of this transcriptional regulator by RT-qPCR upon exposure of wt S. albus to DMSO (con-trol), ivermectin, or etoposide was examined. Both elicitors induced a 2-2.5-fold down-regulation of surR expression (FIG. 7A).

Figure 7B:
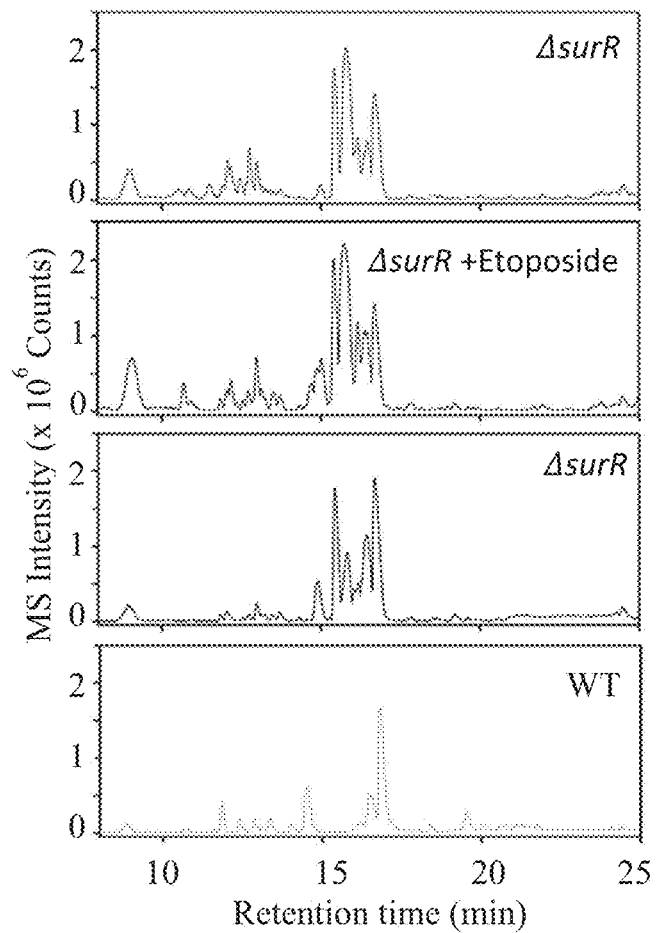
FIG. 7B is a base-peak chromatogram HPLC-MS analysis of the secondary metabolome of wt *S. albus* (bottom), ΔsurR (bottom middle), ΔsurR+etoposide (top middle), and ΔsurR+ivermectin (top).
Figure 7C:
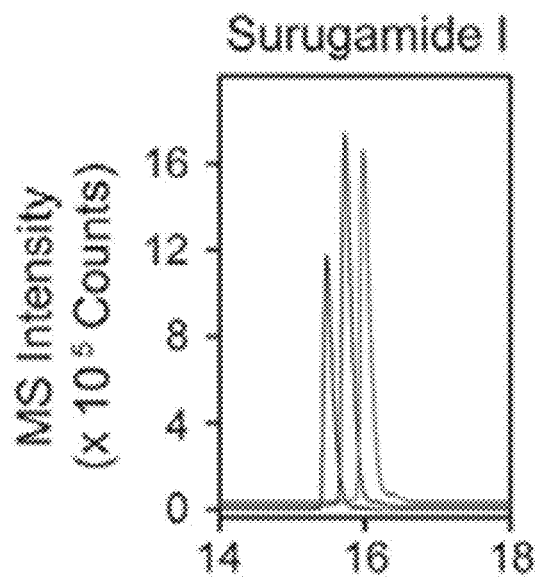
FIG. 7C is a targeted extracted-ion chromatogram surugamide I.
Figures 7D, 7E:
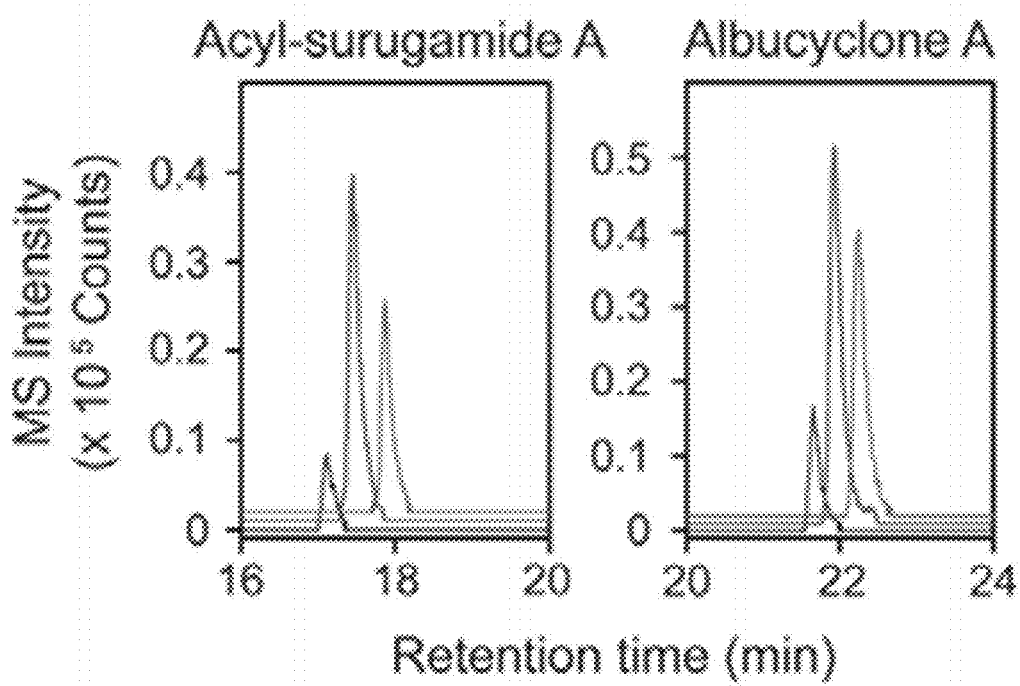
FIG. 7D is a targeted extracted-ion chromatogram acyl-surugamide A.
FIG. 7E is a targeted extracted-ion chromatogram albucyclone A.

If SurR is a transcriptional repressor and thus silences the sur gene cluster, the down-regulation by the elicitors could explain their stimulatory activities. This was tested by deleting surR using insertional mutagenesis (surR::apr, referred to as LlsurR). Subsequently, the secondary metabolome of wt S. albus was compared with that of LlsurR. The mutant displayed a striking overproduction of surugamides, acylsurugamides, albucyclones, and albuquinone A (FIG. 7B). In fact, the secondary metabolome of LlsurR was very similar to that induced by ivermectin or etoposide in wt S. albus. These results are entirely consistent with a role for surR as a repressor or silencer of the sur BGC. They further imply that activation of sur by iver-mectin and etoposide functions, in part, through down-regulation of surR.

To examine whether surR expression is the only regulatory pathway, by which 1 and 2 induce sur, LlsurR was treated with ivermectin or etoposide and the resulting secondary metabolomes were assessed by HPLC-Qtof-MS. A remarkable induction of a variety of metabolites were observed, including many described above (FIG. 7B-7E). The combination of elicitors and LlsurR appeared to have a synergistic effect on secondary metabolite biosynthesis, exhibiting vastly increased production levels compared to LlsurR alone or ivermectin/etoposide treatment of the wt strain. These results indicate that the two elicitors exercise pleiotropic effects and, aside from modulating the transcription of surR, also impinge on other regulatory pathways that result in induction of sur. Treatment of the LlsurR strain with ivermectin or etoposide results in a >35-fold increase in the production of surugamide I. A >40-fold and >50-fold upregulation of the cryptic acyl-surugamide A and albucyclone A is estimated, respectively, based on the lower limits of detection of our HPLC-Qtof-MS. The treatment of LlsurR with 1 or 2 will facilitate efficient production and further characterization of the products of sur in future studies. These results also set the stage for investigating the detailed regulatory circuits that the elicitors affect to induce sur.

Several largely complementary approaches have been developed for inducing silent gene clusters in bacteria. One advantage of the disclosed approach is that any given cryptic gene cluster can be activated in a targeted fashion. By varying elicitors and/or their concentrations, the level of activation can be tuned, and activation levels of up to 150-fold have been achieved, thus greatly enhancing secondary metabolite synthesis from a given silent cluster. Combination of HiTES with traditional gene deletions, that is chemical genetics with classical genetics, further augments the diversity and quantity of the cryptic metabolites, as we show with the treatment of LlsurR with small molecule elicitors. Moreover, the elicitors can be pleiotropic and give rise to numerous other secondary metabolites, thus facilitating small molecule discovery in a global and pathway-specific manner simultaneously. Lastly, with small molecule probes at hand to modulate the expression of a cluster, the regulatory pathways can be examined.

Figure 9:
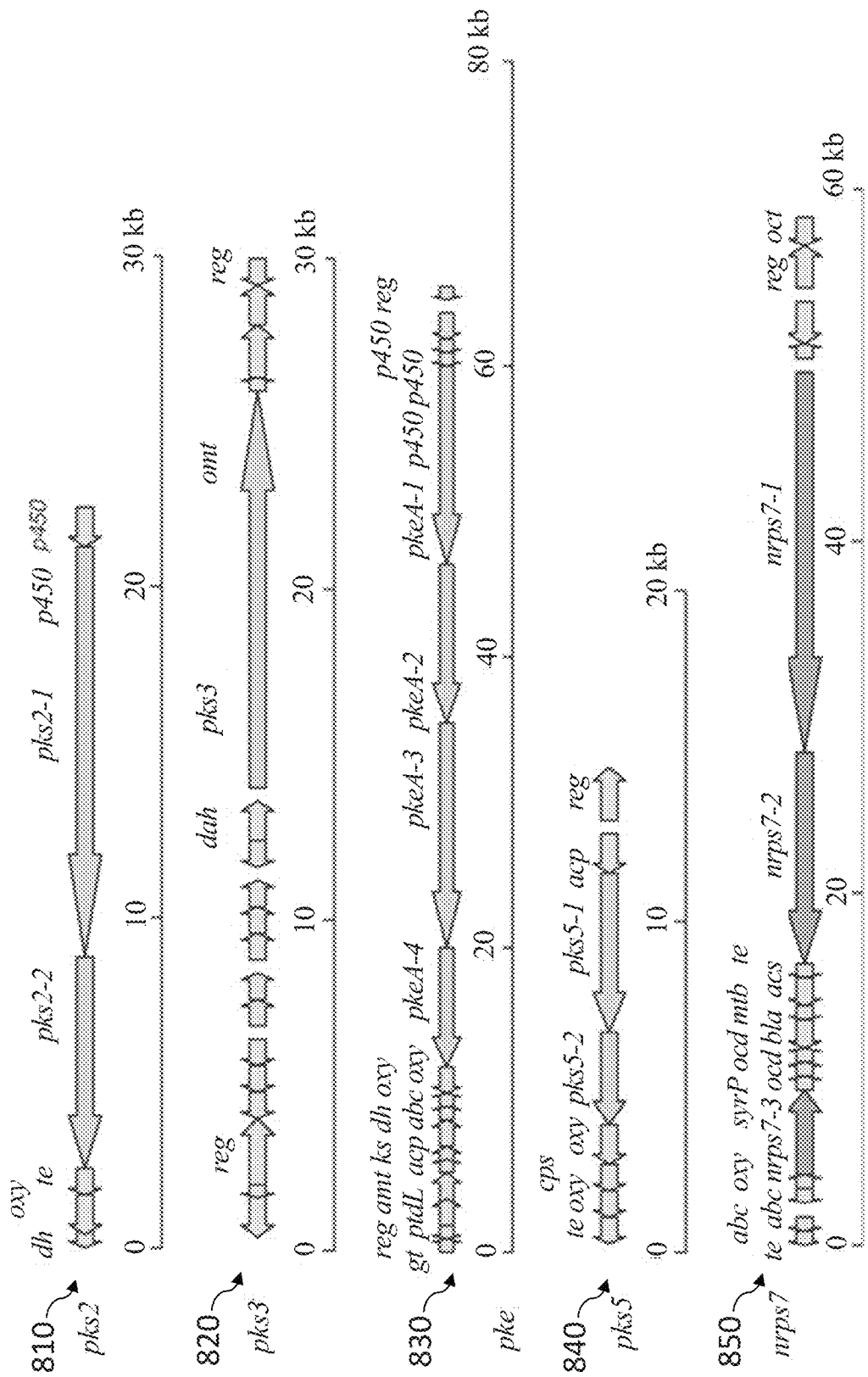
FIG. 9 is a depiction of five gene clusters from *S. erythraea*.
Figure 10:
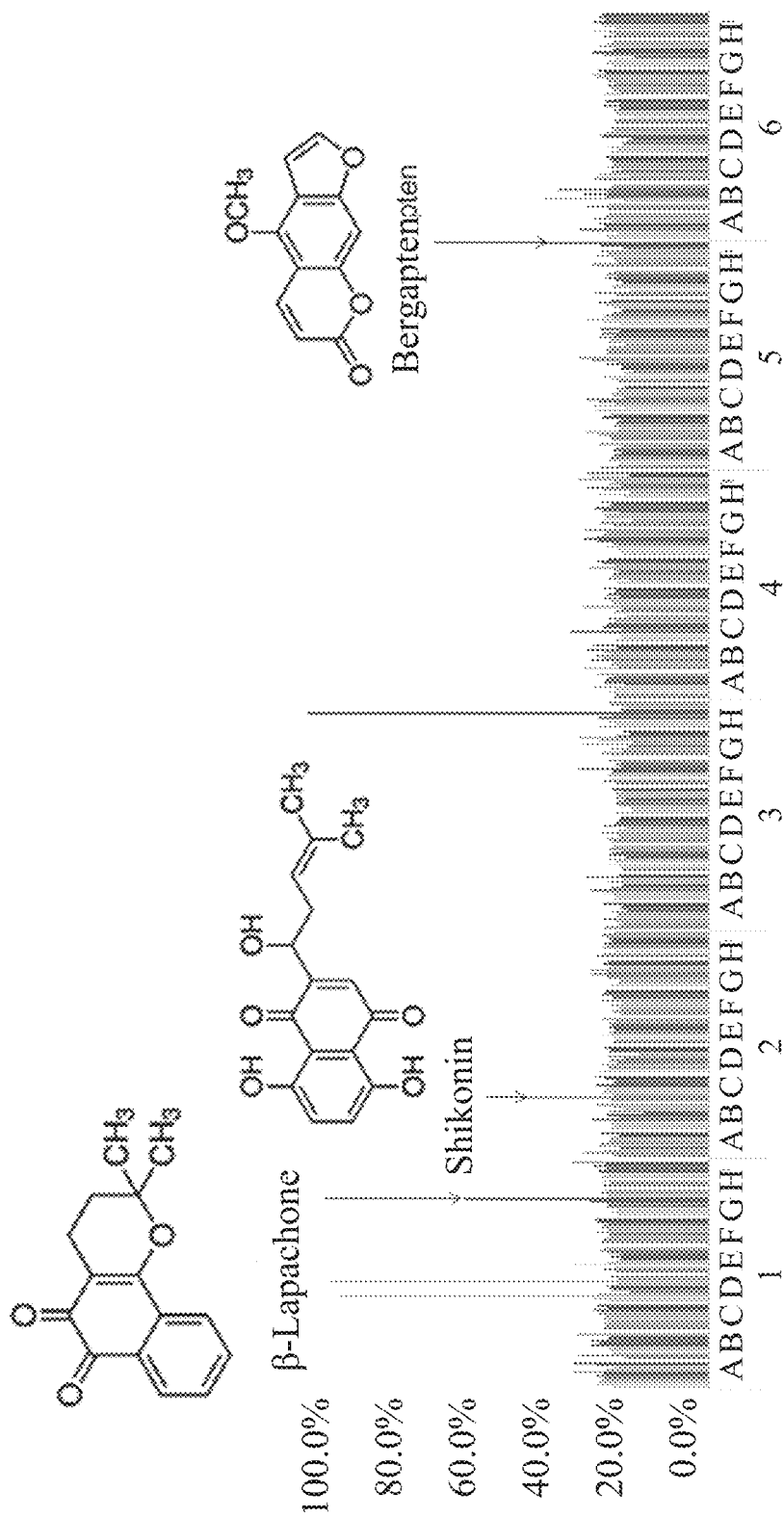
FIGS. 10-14 are graphs of high-throughput elicitor screens to induce the gene clusters from *S. erythraea*.
Figure 11:
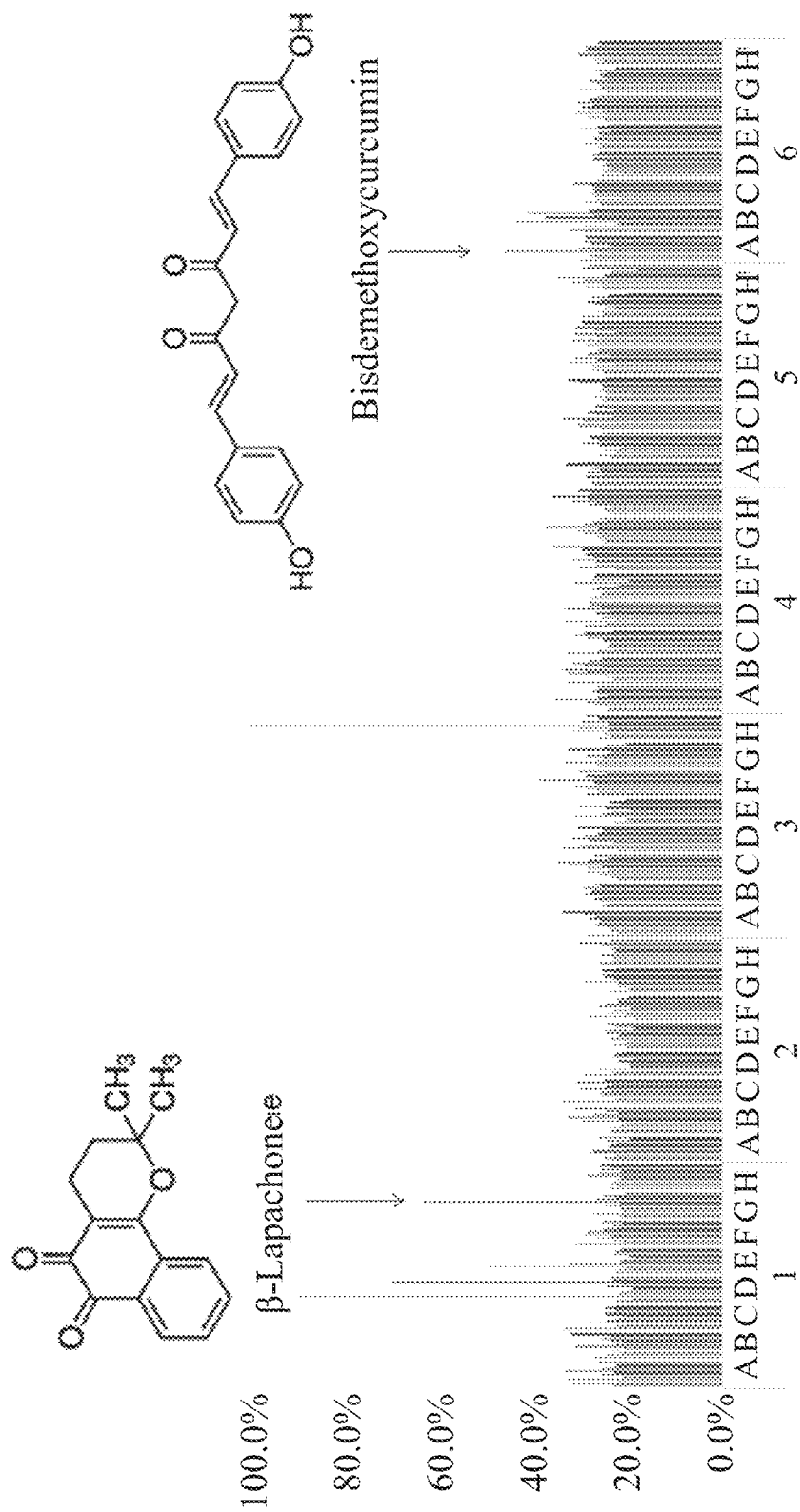
Figure 12:
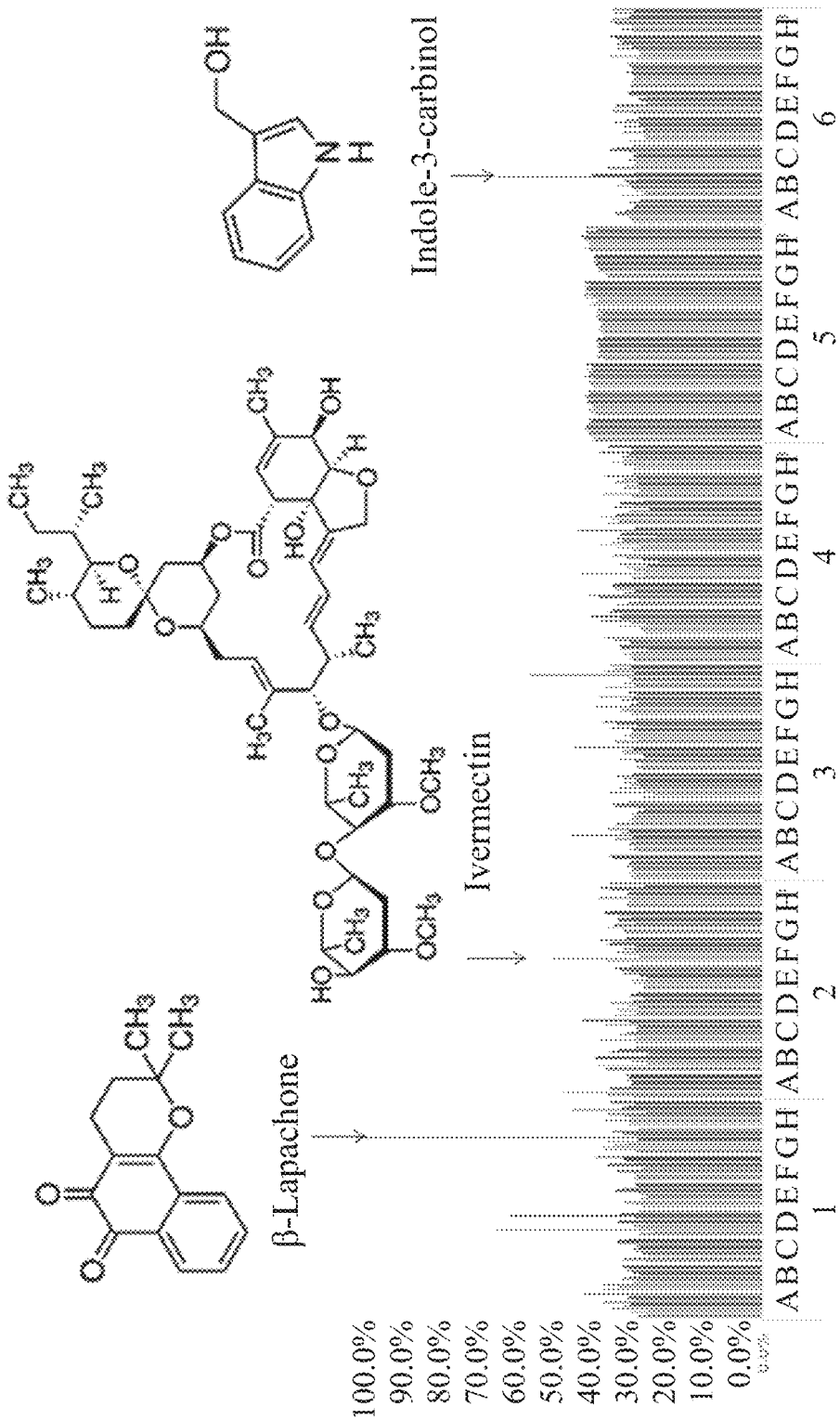
Figure 13:
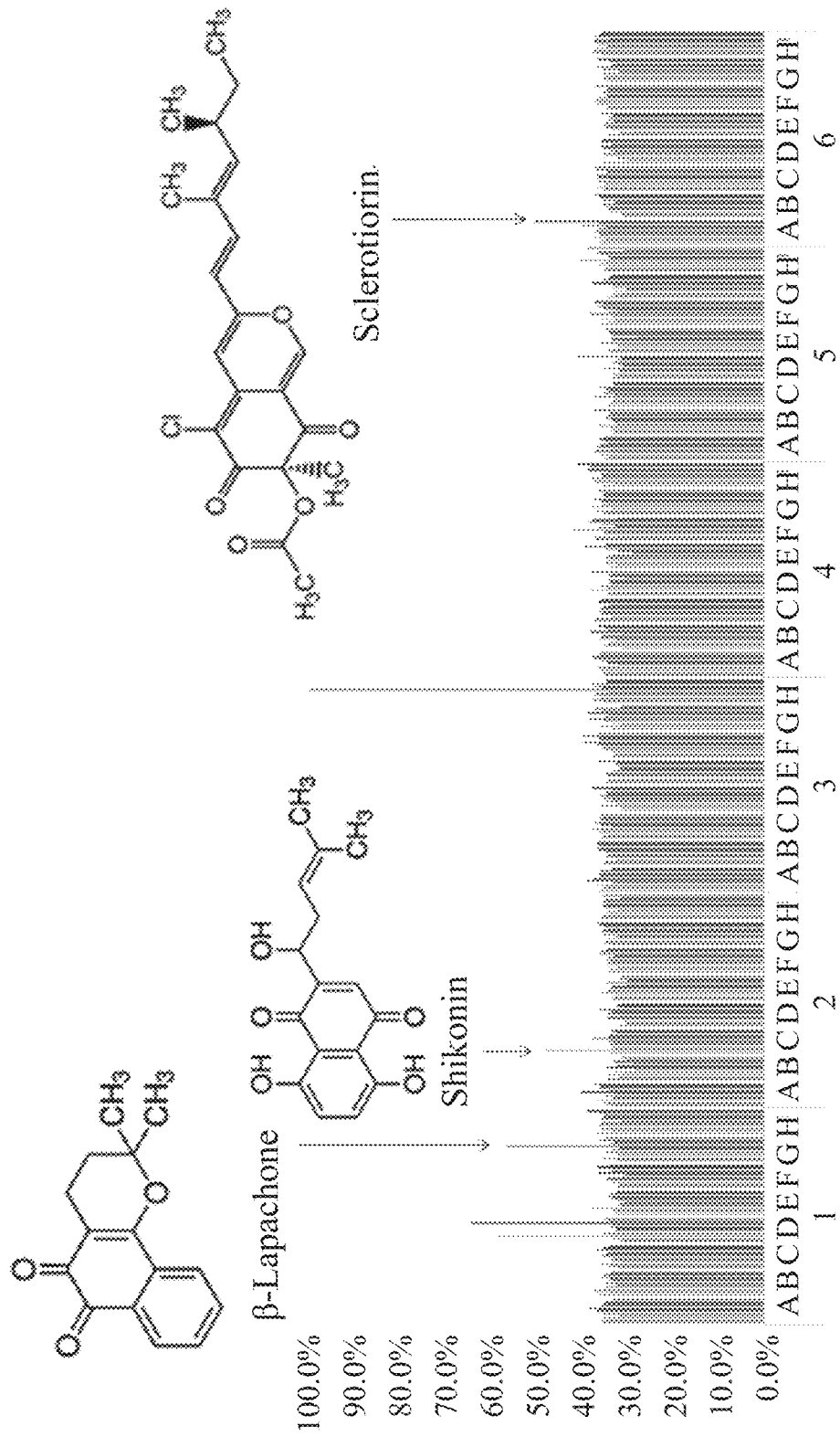
Figure 14:
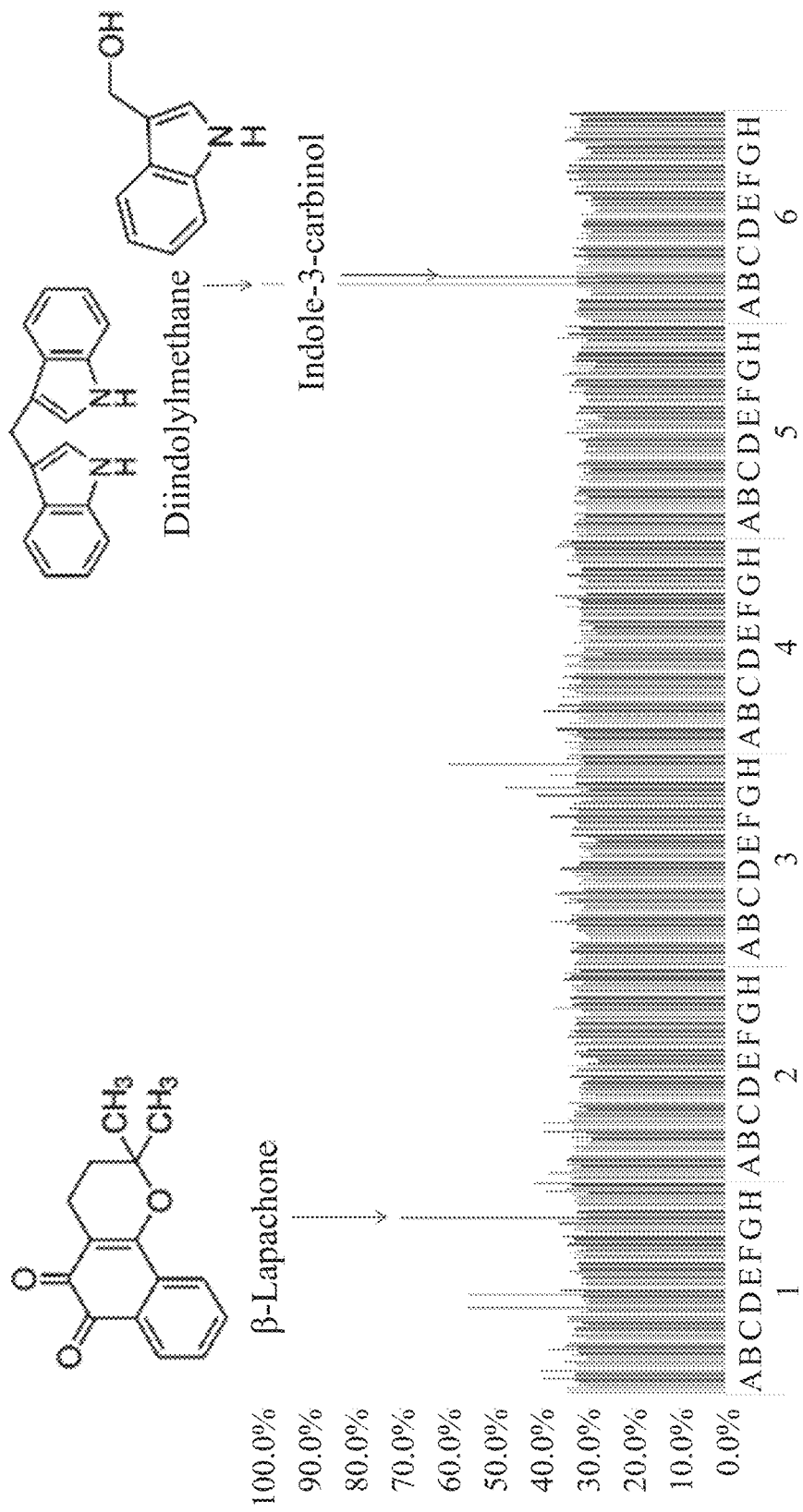

For example, referring to FIG. 9, five gene clusters were activated by HiTES in S. erythraea. Gene cluster 2631 (810), 2875 (820), 4143 (830), 4477 (840), and 4286 (850). The HiTES results can be seen in FIGS. 10-14. The top three elicitors for Gene cluster 2631 (810) can be seen in FIG. 10—beta-Lapachone, Shikonin, and Bergapten. The top two elicitors for Gene cluster 2875 (820) can be seen in FIG.

11—beta-Lapachone, and Bisdemethoxycurcumin. The top three elicitors for Gene cluster 4143 (830) can be seen in FIG. 12—beta-Lapachone, Ivermectin, and Indole-3-carbinol. The top three elicitors for Gene cluster 4286 (840) can be seen in FIG. 13—beta-Lapachone, Shikonin, and Sclerotiorin. The top three elicitors for Gene cluster 4477 (850) can be seen in FIG. 14—beta-Lapachone, Diindolylmethane, and Indole-3-carbinol.

Figure 15:
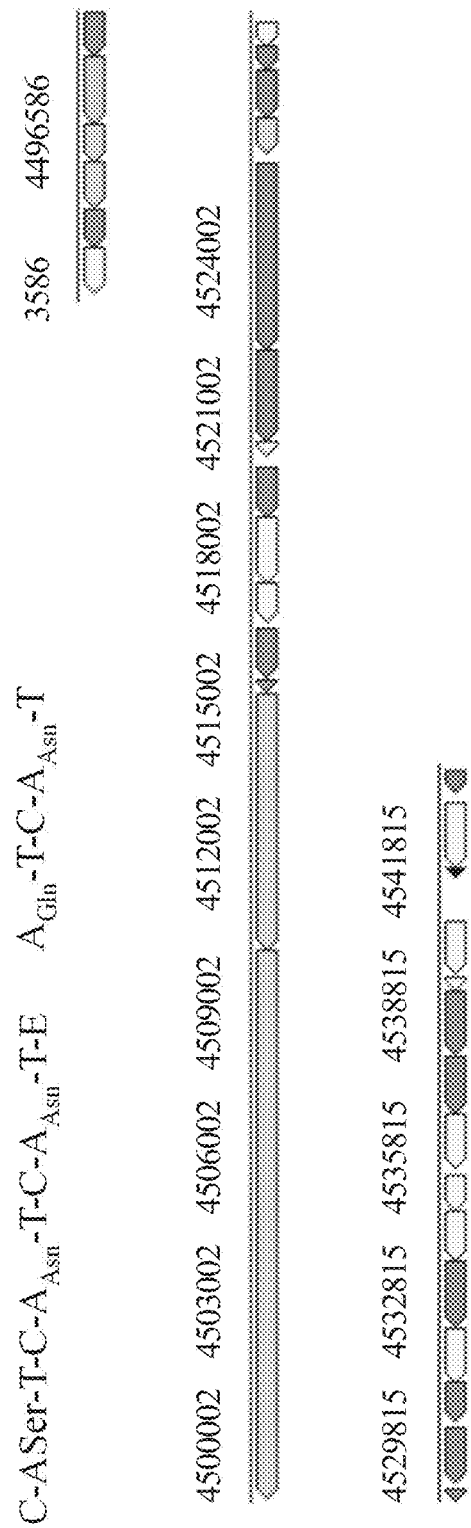
FIG. 15 is a depiction of a gene cluster from *S. avermitilis*.
Figure 16:
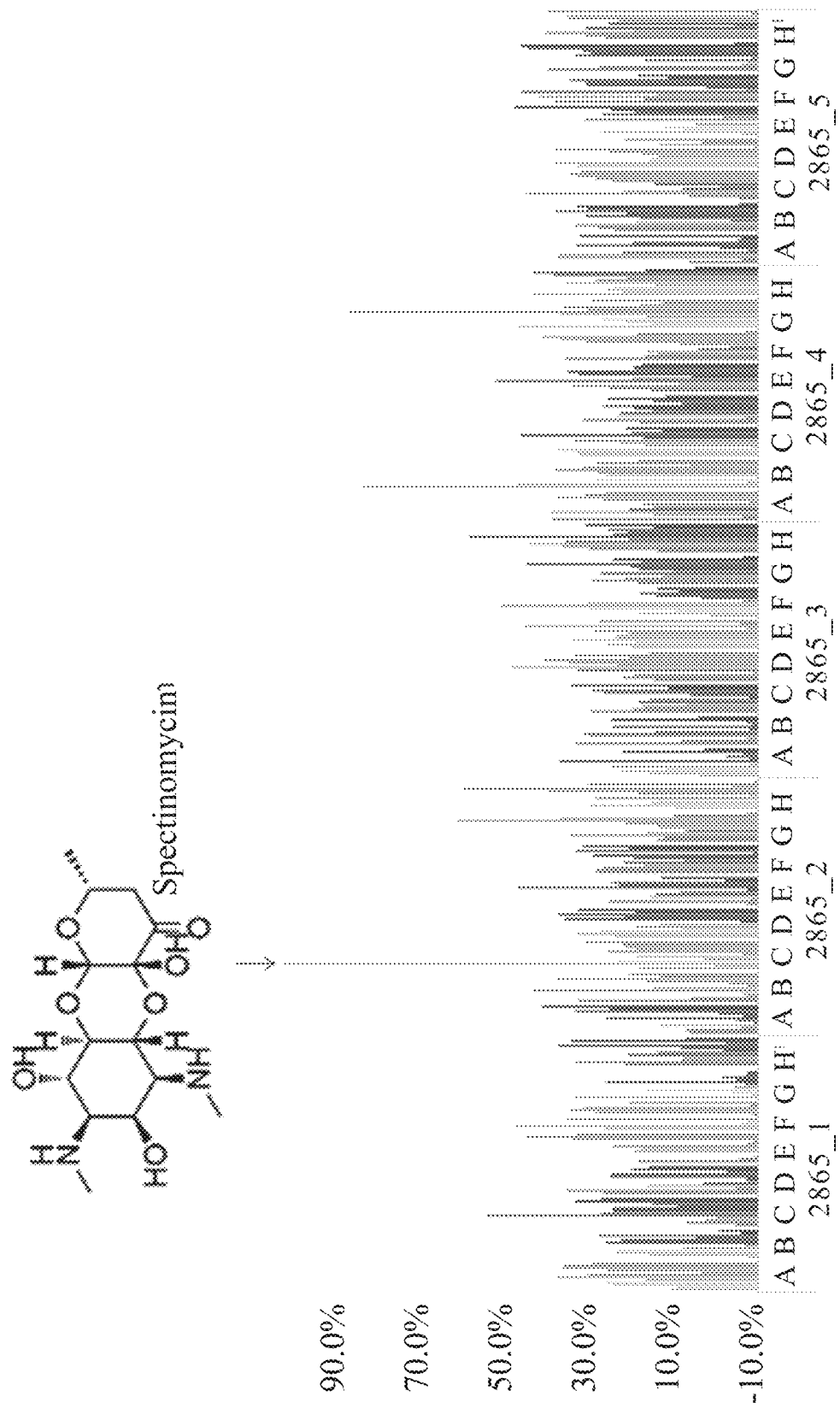
FIGS. 16-17 are graphs of high-throughput elicitor screens to induce the gene clusters from *S. avermitilis*.
Figure 17:
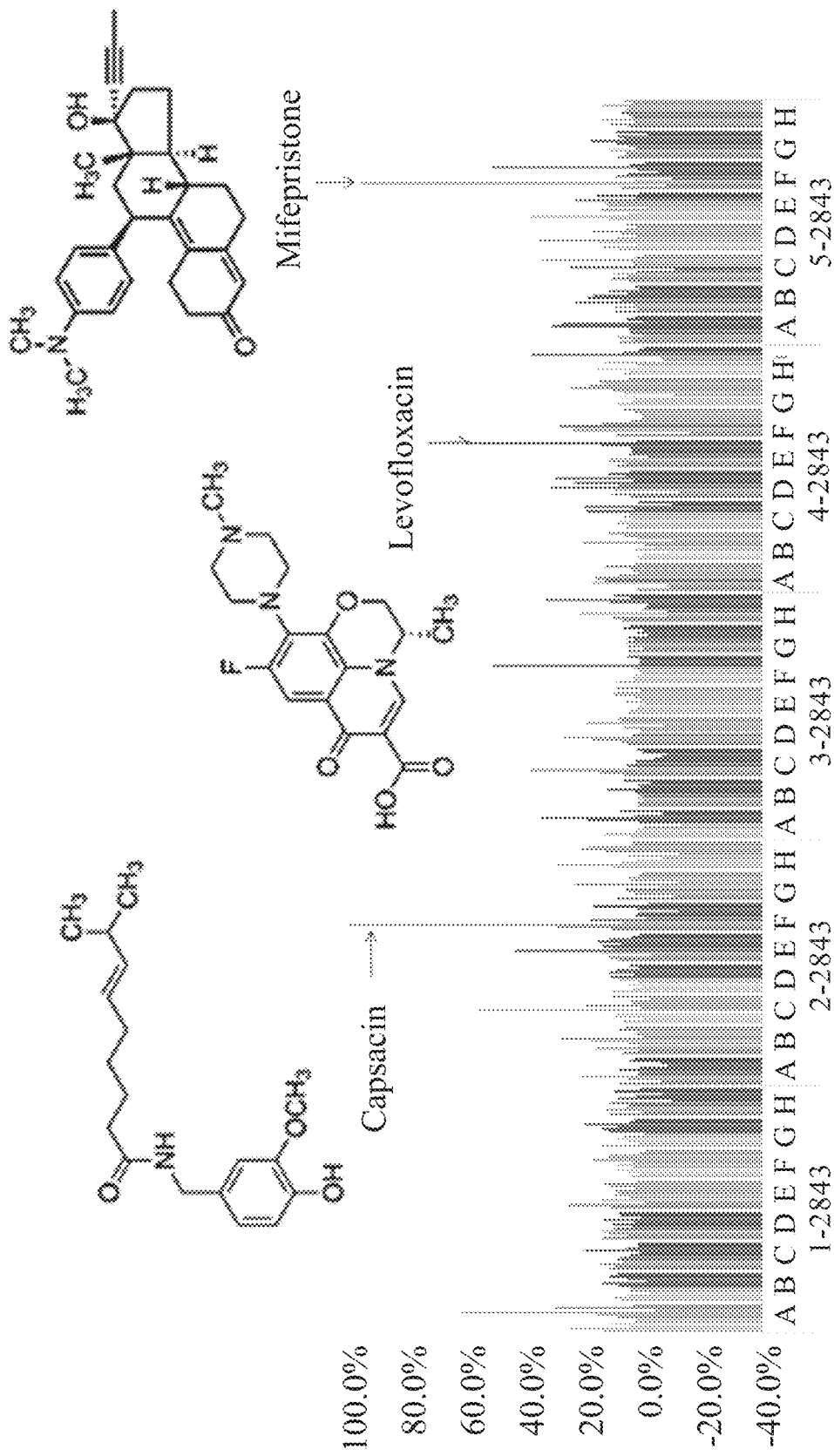

Further, referring to FIG. 15, one gene cluster was activated by HiTES in *S. avermitilis*, gene cluster 3648. The top four elicitors for Gene cluster 3648 can be seen in FIGS. 16 and 17. A first HiTES result with a first set of molecules resulted in a single elicitor being identified—Spectinomycin (See FIG. 16). A second HiTES result with a second set of molecules resulted in three additional elicitors being identified—Capsacin, Levofloxacin, and Mifepristone (See FIG. 17).

Figure 18A:
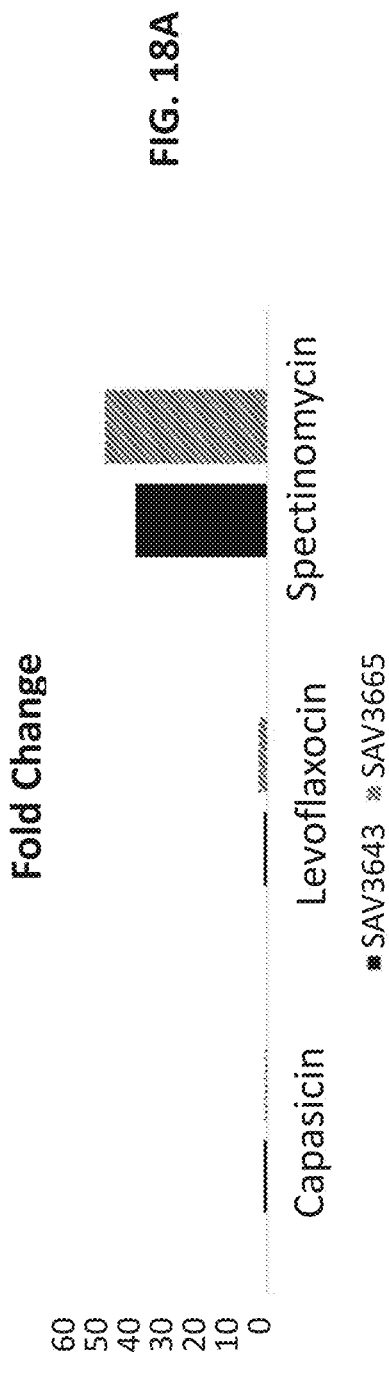
FIG. 18A is a graph of the expression of two genes in *S. avermitilis* using different elicitors.

As seen in FIG. 18A, the expression of two genes (SAV3643 and SAV3665) in cluster 3648 of *S. avermitilis* were measured by RT-qPCR using elicitors capsaicin, levofloxacin, and spectinomycin (each at a final concentration of 5 ug/mL). Spectinomycin showed the highest level of upregulation at 40-50-fold, relative to untreated samples.

Figure 18B:
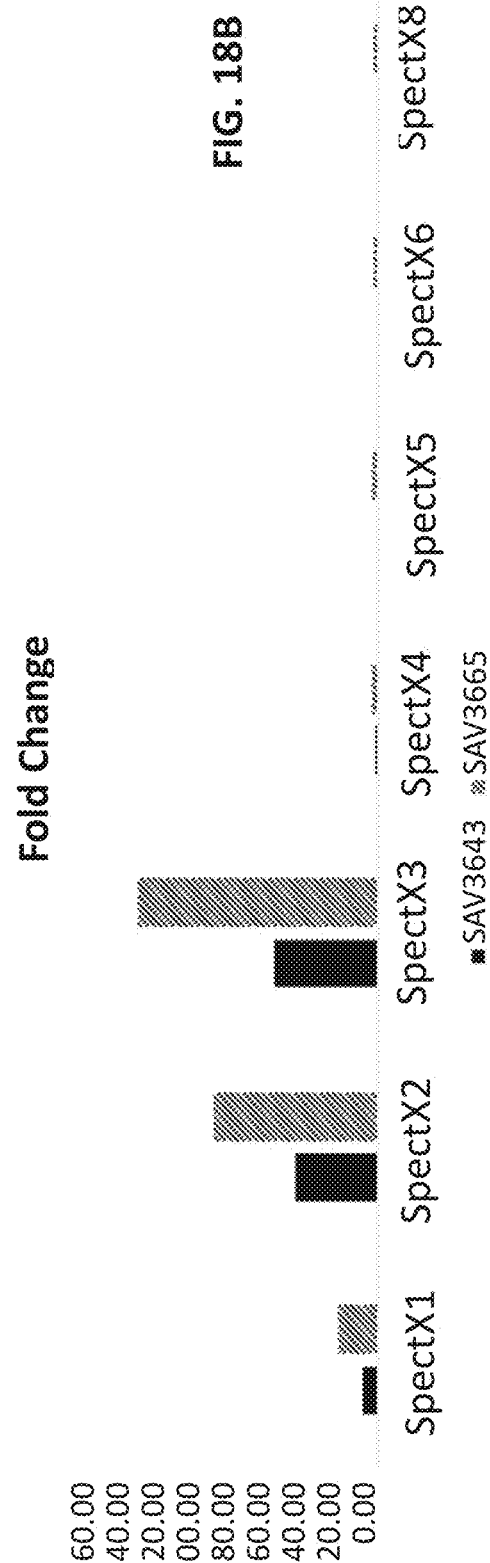
FIG. 18B is a graph of the expression of two genes in *S. avermitilis* using different concentrations of a single elicitor.

Similarly, referring to FIG. 18B, a dose-response analysis was compiled of the expression of those two genes in cluster 3648 of *S. avermitilis* with spectinomycin. "SpectX1" (the left-most item on the x-axis in FIG. 18B) corresponds to a concentration of 2.5 ug/mL. Moving to the right, each item refers to use of spectinomycin at a 2.5 ug/mL increase over the previous item. Thus, "SpectX2" is 5 ug/mL, "SpectX3" is 7.5 ug/mL, etc. A clear dose-response is observed. Similar behavior as was seen with other antibiotics occurred here as well—concentrations greater than a threshold here, greater than 7.5 ug/mL inhibited growth.

Methods

Bacterial Strains and Plasmids

The wild type strain of *Streptomyces albus* J1074 was kindly provided by the laboratory of Prof. Roberto Kilter at Harvard Medical School (Boston, Mass.). eGFP was kindly provided by the laboratory of Prof. Zenner Gitai at Princeton University (Princeton, N.J.). *E. coli* strains ET12567 and BW251.13, and plasmids pSET152, pIB139 and pJTU1289 were kindly provided by the laboratory of Prof. Zixin Deng at Shanghai Jiao Tong University (Shanghai, China). XylE was kindly provided by the laboratory of Prof. Mervyn Bibb at the John Innes Centre (Norwich, UK).

DNA Manipulation and Construction of Mutants

To generate the *S. albus* attB::$P_{ermE}$-eGFP reporter constructs, an eGFP fragment without a ribosomal binding site (RBS) was amplified by PCR using the corresponding primers (Table 2).

TABLE 2

Strains and plasmid used and generated:

| Strain/Plasmid | Purpose | Source |
| --- | --- | --- |
| *E. coli* DH5α | Host strain for cloning | NEB |
| *E. coli* BW25113 | Host strain for PCR targeting method | Deng Lab |
| *E. coli* ET12567 | Donor strain for conjugation | Deng Lab |
| *E. coli* K12 | Test strain for bioactivity assay | Kolter Lab |
| *Bacillus subtilis* 168 | Test strain for bioactivity assay | ATCC |
| *Pseudomonas aeruginosa* PA01 | Test strain for bioactivity assay | ATCC |
| *Staphylococcus aureus* Newman | Test strain for bioactivity assay | ATCC |
| *Enterococcus faecalis* 0G1RF | Test strain for bioactivity assay | Kolter Lab |
| *Saccharomyces cerevisiae* | Test strain for bioactivity assay | Kolter Lab |
| *Saccharomyces pombe* | Test strain for bioactivity assay | Zakian Lab |
| *Streptomyces albus* J1074 | Wild type strain | Kolter Lab |
| surA::apr (ΔsurA) | surA inactivation mutant of *S. albus* J1074 | This study |
| surB::apr (ΔsurB) | surB inactivation mutant of *S. albus* J1074 | This study |
| surR::apr (ΔsurR) | surR inactivation mutant of *S. albus* J1074 | This study |
| surE::eGFPx3 | eGFP reporter for sur cluster | This study |
| attB::Psur-eGFPx3 | Neutral site eGFP reporter of sur cluster | This study |
| attB::Psur-XylE | Neutral site xylE reporter of sur cluster | This study |
| attB::PermE-XylE | Positive control: PermE-controlled xylE reporter | This study |
| attB::PermE-eGFP | Positive control: PermE-controlled eGFP reporter | This study |
| attB::PermE-eGFPx3 | Positive control: PermE-controlled eGFPx2 reporter | This study |
| attB::PermE-eGFPx3 | Positive control: PermE-controlled eGFPx3 reporter | This study |
| PSET152 | AprR, Vector for neutral site insertion | Deng Lab |
| pIB139 | AprR, Vector for neutral site insertion with PermE | Deng Lab |
| pSK+ | AmpR, cloning vector cloning | Deng Lab |
| pJTU1278 | AmpR, TsrR, conjugation vector | Deng Lab |
| pJTU1289 | AmpR, TsrR, conjugation vector | Deng Lab |
| pIJ773 | AprR, Vector for PCR targeting method | Deng Lab |
| pΔsurA | AmpR, TsrR, AprR, plasmid used for surA inactivation | This study |
| pΔsurB | AmpR, TsrR, AprR, plasmid used for surB inactivation | This study |
| pΔsurR | AmpR, TsrR, AprR, plasmid used for surR inactivation | This study |
| pAttP::Psur-xylE | AprR, plasmid for neutral site insertion of PsurE-XylE | This study |

TABLE 2-continued

Strains and plasmid used and generated:

| Strain/Plasmid | Purpose | Source |
| --- | --- | --- |
| pAttP::Psur-eGFPx3 | AprR, plasmid for neutral site insertion of Psur-eGFPx3 | This study |
| pAttP::PermE-xylE | AprR, plasmid for neutral site insertion of PermE-xylE | This study |
| pAttP::PermE-eGFP | AprR, plasmid used neutral site insertion of PermE-eGFP | This study |
| pAttP::PermE-eGFPx2 | AprR, plasmid used neutral site insertion of PermE-eGFPx3 | This study |
| pAttP::PermE-eGFPx3 | AprR, plasmid used neutral site insertion of PermE-eGFPx3 | This study |
| pSurE::eGFPx3 | AprR, plasmid used replacement of surE with eGFPx3 | This study |

The PCR fragment was digested with NdeI/EcoRl, along with plasmid pIB139, which contains the ermE promoter element. After ligation and amplification in *E. coli* DH5a, pAttP::$P_{ermE}$-eGFP was obtained (Table 1). This plasmid was digested with EcoRl. A second copy of eGPP containing an RBS was PCR-amplified with appropriate primers (Table 2) and digested with MfeI/EcoRl. Ligation into pAttP::$P_{sur}$-eGFP afforded pAttP::$P_{ermE}$-eGFPx2. This process was repeated to give pAttP::$P_{ermE}$-eGFPx3. A similar strategy was used in making pAttP::$P_{ermE}$-xylE reporter integration plasmids. In this case, the xylE fragment was PCR-amplified from pIJ4083 using the primers shown (Table S2). The plasmids pAttP::$P_{ermE}$-eGFP, pAttP::$P_{ermE}$-eGFPx2, pAttP::$P_{ermE}$-eGFPx3, and pAttP::$P_{ermE}$-xylE were transformed into *E. coli* ET12567 by heat shock (see Table S1). Conjugation into *S. albus* was carried out as described below.

To generate *S. albus* $P_{sur}$-eGFP constructs, the $P_{sur}$ promoter region (~260 bp) upstream of surE was selected using the BPROM website: (http://www.softberry.com/berry.phtml?topic=bprom&group=programs&subgroup=gfindb).

This region ($P_{sur}$), along with xylE and eGFP were PCR-amplified and adjoined using overlap extension PCR to generate $P_{sur}$-xylE and $P_{sur}$-eGFP. These were cloned into plasmid pSET152, and subsequently, two additional copies of eGFP were added from MfeI/EcoRl-digested fragments, as described above, thus yielding plasmids pAttP::$P_{sur}$-eGFPx3 and pAttP::$P_{sur}$-xylE (see Table 1). These two plasmids were transformed into *E. coli* ET12567 by heat shock and conjugation into *S. albus* carried out as described below.

To generate the surE::eGFPx3 reporter construct, a ~2 kb region upstream of surE was amplified with the appropriate primers (Table 2). Then overlap extension PCR was carried out to fuse this fragment with eGFP This construct was cloned into pJTU1278 using restriction enzymes BamHl and EcoRl. Subsequently, two additional eGFP copies, amplified and digested with MfeI/EcoRl, were added as described above. Finally, a ~2 kb region downstream of surE was amplified with appropriate primers (Table 2), digested with EcoRl/HindIII, and ligated into the vector containing the upstream region of surE adjoined to eGFPx3, to give pSurE::eGFPx3 (see Table 1). This plasmid contains the proper construct consisting of 2 kb regions up- and down-stream of surE, with three copies of eGFP in the middle and was used for chromosomal replacement of surE with three copies of eGFP. The plasmid was transformed into *E. coli* ET12567 by heat shock and conjugation was carried out as described below.

To create the surR gene replacement plasmid (pΔsurR, see Table 1), ~2 kb regions up- and down-stream of surR were amplified using appropriate primers (Table 2) and digested with XbaI and HindIII. Each fragment was in turn cloned into pIJ2581 to create a contiguous 2 kb inserted fragment with a HindIII restriction site in the middle. The plasmid was amplified in *E. coli* DH5a and digested with HindIII. The apramycin resistance gene (apr) fused to oriT was amplified by PCR with appropriate primers from vector pIJ773. This was then digested with HindIII and ligated into the pIJ2581 vector containing the 2 kb insert, thus yielding the pIJ2581 construct containing a fragment that comprises 2-kb-up-surR_oriT-apr_2-kb-dn-surR, which was used for generating the surR::apr gene inactivation mutant as described below. This plasmid (pΔsurR) was transformed into *E. coli* ET12567 by heat shock and conjugation performed as outlined below.

For generating the surA and surB gene replacement plasmids (pΔsurA and pΔsurB, see Table 1), the PCR-targeting gene replacement strategy was employed according to standard protocols. Briefly, a 4.8 kb internal fragment of surA was amplified by PCR, ligated into pJTU1289 (Tsr$^R$), and subsequently transformed into *E. coli* BW25113, which contains the λ Red plasmid pIJ790, to give pJTU1289-surA_int. A separate linear fragment was generated containing a fused oriT-apr (obtained from pIJ773) flanked by 40 bp regions that were homologous to internal regions of surA (about 700 bp apart). Electrocompetent *E. coli* BW25113 containing pJTU1289-surA_int and pIJ790 were cultured in LB in the presence of a final concentration of 10 mM L-arabinose to an OD$_{600\,nm}$ of 0.4-0.6 at 30° C. and then electrotransformed with the linear fragment. Apramycin-resistant colonies were selected on LB-Agar containing 50 µg/mL apramycin. The correct construct was verified by restriction endonuclease and DNA gel electrophoresis analysis. A similar strategy was used to generate the surB gene replacement plasmid. The plasmids (pΔsurA and pΔsurB) were transformed into *E. coli* ET12567 by heat shock and conjugation performed as described below.

Conjugation of all the plasmids into *S. albus* used the following protocol: The plasmids (Apr$^R$) were all transformed into *E. coli* ET12567 (Cm$^R$) containing pUZ8002 (Kan$^R$), as described above. Conjugation was performed using the spores of *Streptomyces albus* J1074 (grown on SFM medium) according to standard methods. Briefly, *E. coli* ET12567 containing the desired plasmids was cultured in LB containing Apr (50 µg/mL), Kan (50 µg/mL), and Cm (25 µg/mL) to an OD$_{600\,nm}$ of ~0.4. The cells were collected by centrifugation and washed with LB to remove the antibiotics. *S. albus* spores were washed with TES buffer (50 mM, pH 8.0), collected, resuspended in 500 µL TES buffer, and heat shocked at 50° C. for 10 min. Spore stock was then supplemented with 500 µL of 2× spore activating media, and then cultured at 37° C. for 2 h. The spore stocks and *E. coli* donor cells were collected and resuspended in equal amounts of LB media and subsequently mixed together. They were then plated on SFM agar plates (2% soybean meal in tap water, sterilized by autoclave, then filtered and mixed with 2% mannitol and 2% agar, and then autoclaved again) and grown for 16-20 h. The attB-integration mutant exconjugants were selected with 35 µg/mL Apr and 50 µg/mL Tmp (trimethoprim), while the double-crossover knockout mutant exconjugants were selected with 25 µg/mL Tsr, 35 µg/mL Apr, and 50 µg/mL Tmp. For the attB-insertion, mutants were verified by PCR. For double-crossover mutants, exconjugants were first cultured in TSBY medium without any antibiotics. Surviving cells were sub-cultures again in TSBY medium. They were then diluted to obtain single colonies on SFM agar plates. The colonies were tested individually and separately for Apr-resistance and Tsr-susceptibility. The desired mutants were verified by PCR.

High-Throughput Elicitor Screen

Seed cultures for the reporter strains sur::eGFPx3, attB::$P_{sur}$-eGFPx3, negative control wild-type, and positive control attB::$P_{ermE}$-eGFPx3 inoculated by transferring fresh spores (~$10^7$) into 20 mL of YEME medium (per L: 3% (w/v) yeast extract, 5% peptone, 3% malt extract, 1% glucose and 10.7% sucrose, and 5 mM $MgCl_2.6H_2O$) in a 125 mL Erlenmeyer flask equipped with stain-less steel springs. The cultures were grown at 30° C. and 250 rpm for 3 days. Mycelia from each of the four cultures were collected by centrifugation (10 min, 3000 g, RT) and diluted into 150 mL of R4 medium to give a final concentration of 0.05% (w/v). R4 medium consisted of (per L) 0.5% (w/v) glucose, 0.1% yeast extract, 0.5% $MgCl_2.6H_2O$, 0.2% $CaCl_2.2H_2O$, 0.15% proline, 0.118% valine, 0.28% TES, 50 mg/L casamino acid, 100 mg/L $K_2SO_4$, and 1× trace element solution, which contains 40 mg/L $ZnCl_2$, 200 mg/L $FeCl_3.6H_2O$, 10 mg/L $CuCl_2.2H_2O$, 10 mg/L $MnCl_2.4H_2O$, 10 mg/L $Na_2B_4O_7.10H_2O$, and 10 mg/L $(NH_4)_6Mo_7O_{24}.4H_2O$).

Subsequently, the two reporter strains (sur::eGFPx3 and attB::$P_{sur}$-eGFPx3) were each dispensed into 5× sterile, clear-bottom 96-well plates (150 µL per well) using a MultiFlo Microplate Dispenser (BioTek). A separate sterile 96-well separate plate was prepared for positive and negative controls; it contained the negative control (wt *S. albus* J1074) in columns 1-3, sur::eGFPx3 in columns 4-6, attB::$P_{sur}$-eGFPx3 in columns 7-9, and the positive control attB::$P_{ermE}$-eGFPx3 in columns 10-12 of the plate. No elicitors were added to the control plates. For strains sur::eGFPx3 and attB::$P_{sur}$-eGFPx3, candidate elicitors were added from a 502-member Natural Products library (Enzo Scientific) using a CyBi-Well automated liquid transfer robot (CyBio). A volume of 0.4 µl was transferred from the compound library into each well to give a final concentration of ~33 µM. Upon additional of the compound library, t=0 fluorescence reads were recorded on a Synergy H1MF plate reader (BioTek) using $A_{ex}$=485 nm and $A_{em}$=505-650 nm in 5 nm steps. The plates were then sealed with an air-permeable membrane and the plates incubated at 30° C. and 250 rpm for 60 h in Multitron Shaker (ATR) equipped with green sealing trays. To maintain constant humidity, several 1-1 Erlenmeyer flasks containing 200 ml of water were also placed inside the shaker. After 60 h, end-point fluorescence was determined as described above. Fluorescence emission at 514 nm at 60 h was subtracted from that at t=0 and the data normalized to the fluorescence intensity of the positive control to give the plots depicted in FIG. 3.

Z' scores was calculated according to Eq. 1, where $o_p$ and $o_n$ correspond to the standard deviation in fluorescence emission for the positive (attB::$P_{ermE}$-3XeGFP) and negative (sur::3XeGFP or attB::$P_{sur}$-3XeGFP in the absence of elicitors) controls, respectively, and $\mu_p$ and $\mu_n$ correspond to the mean fluorescence emission for the positive and negative controls among the replicates.

$$Z'=1-\{3\times(o_p+o_n)/(\mu_p-\mu_n)\} \tag{Eq. 1}$$

Reverse Transcription Quantitative PCR

All operations involving RNA utilized a dedicated RNase-free work area. To commence the experiment, seed cultures of wt *S. albus* J1074 were prepared by inoculating 3 ml of TSBY medium (3% (w/v) tryptic soy broth and 0.5% yeast extract) in a sterile 14 ml bacterial culture tube with freshly-prepared spores (~$10^7$). The culture was incubated at 30° C. and 250 rpm in an Ecotron Shaker (ATR). After 48 hours cultivation, the cells were collected by centrifugation and subsequently diluted to a final concentration of 0.05% (w/v) in 250 ml Erlenmeyer flask containing 50 ml of R4 medium. Desired elicitors were added to final concentrations indicated in the figures (typically 1-100 µM), and the cultures were incubated at 30° C. and 250 rpm. After 48 h, 1 ml was removed from each sample and transferred to a 1.5 ml RNase-free Eppendorf tube (Ambion). Each sample was centrifuged (16,000 g, 3 min) to collect the cells, the supernatant discarded, the cells flash-frozen in liquid $N_2$, and stored at –80° C.

RNA isolation was carried out using the Qiagen RNeasy kit following the manufacturer's instructions without modifications. Upon isolation, contaminating DNA was removed using the DNA-free kit (Ambion) according to manufacturer's instructions. Gel electrophoreses subsequently confirmed RNA integrity (FIG. S2). Finally, total RNA was converted into cDNA via the PrimeScript™ RT reagent Kit (Takara) using random hexamers as primers and 500 ng of each RNA sample as template.

Three genes (surA, surC and surR) were chosen for quantification by RT-qPCR. The primers were designed using primer-3-plus software available online. The primers were carefully chosen to give an amplicon length of 130-160 bp and a melting temperature of 60° C., though this was later optimized (see below and Table 2). The primers were chosen to vary in length between 18-22 bp, and, if possible, to contain a single G/C clamp at the 3' end. To ensure optimal qPCR parameters, the genomic DNA of *S. albus* J1074 was isolated using the Wizard genomic DNA purification kit (Promega), and each amplicon was subsequently amplified using standard PCR conditions with a high-fidelity, proof-reading Q5 DNA polymerase (NEB). The PCR reactions were then separated on a 1.2% agarose gel, the amplicon excised, and gel-extracted with the Gel Extraction kit (Qiagen). The extracted DNA was used to optimize qPCR conditions. Using the amplicon template, the primer concentrations were first varied followed by the annealing/extension temperatures, which ranged from 58-68° C. in eight steps. The combination that gave the lowest quantification cycle (Cq) was used in the experiments (Table 2). The Cq was obtained with an automatic baseline determined by the CFX Manager Software (Bio-Rad). As positive controls, these standards were included in every plate that contained the experimental samples, along with no-DNA controls, in duplicates.

qPCR analysis was performed on a CFX96 Real-Time PCR Detection System (Bio-Rad) consisting of a C1000 Thermal Cycler and a CFX96 Real-Time System. The reaction was carried out in hard-shell, clear 96-well qPCR plates (Bio-Rad) and utilized the iTaq Universal SYBR Green Supermix (Bio-Rad). Each well, in a total volume of 16 µL, contained 8 µL of iTaq Supermix, 1 µL of standard DNA or cDNA, 1 µL of each primer and 5 µL of DEPC-treated water (Invitrogen). The PCR cycle consisted of 1-min incubation at 95° C. followed by 42 cycles of a 2-step amplification protocol (5 s at 95° C., then 30 s at annealing/extension temperature). This was followed by a denaturation cycle to determine the melting temperature of the amplicon, where a single species was observed in all experiments reported.

Relative quantification was used to determine the levels of each transcript as a function of elicitor. The $C_q$ for each sample was determined in triplicates. The resulting value was then normalized using internal standard GAPDH and further normalized to the DMSO control sample to give the fold-change for that amplicon as a function of elicitors shown in FIG. 2C. The concentrations of elicitors used are indicated in the figure legend.

Small-Scale Fermentation and Work-Up of S. albus J1074

For comparative small-scale fermentations, mutant and wt strains were grown side-by-side in the same media and worked up in identical fashion. Seed cultures of wt S. albus J1074 were prepared by inoculating 3 mL of TSBY medium in a sterile 14 mL bacterial culture tube with freshly-prepared spores (~$10^7$). The culture was incubated at 30° C. and 250 rpm for 2-3 days, then diluted into 50 mL of R4 medium (in a 250 mL Erlenmeyer flask) to a final concentration of 0.05% (w/v). Elicitors were added to the R4 medium at the start of growth at desired concentrations (indicated in figure legends). The cultures were grown at 30° C. and 200 rpm. After ~4 days, cells were removed by centrifugation and the resulting supernatant was extracted twice with 30 mL of ethyl acetate. The organic phases were combined, dried in vacuo, dissolved in 100 µL MeOH and analyzed by low-resolution HPLC-ESI-MS and/or high-resolution (HR) HPLC-Qtof-MS.

Low-Resolution and High-Resolution HPLC-MS and HPLC Systems

Low-Resolution and High-Resolution HPLC-MS

Low resolution (LR) HPLC-MS analysis was performed on an Agilent 1260 Infinity Series HPLC system equipped with an automated liquid sampler, a diode array detector, and a 6120 Series ESI mass spectrometer using a reversed phase Luna C18 column (Phenomenex, 5 µm, 150×4.6 mm). The mobile phase consisted of water and MeCN (both contained 0.1% formic acid). Upon injection, elution was carried out isocratically with 10% MeCN (3 min) followed by a linear gradients from 10%-90% MeCN over 20 min, and 90-100% MeCN over 5 min, at a flow rate of 0.6 mL/min. HR HPLC-MS and HR-tandem HPLC-MS were carried out on an Agilent 6540 UHD Accurate Mass Q-tof LC-MS system, which consists of a 1260 Infinity Series HPLC system, an automated liquid sampler, a diode array detector, a Jet-Stream ESI source, and the 6540 Series Q-tof. The MS was calibrated to <1 ppm. Samples were resolved on the same Luna C18 column under the same gradient program as described above with a flow rate of 0.4 mL/min.

HPLC Purification Systems

HPLC purifications were carried out on an Agilent preparative HPLC system containing a 1260 Infinity series binary pump, a diode array detector, and an automated fraction collector. Semi-preparative or analytical-scale purifications were performed on an Agilent HPLC system containing a 1260 Infinity Series binary pump or a 1290 Infinity quarternary pump. Each system was equipped with an automatic liquid sampler, a temperature-controlled column compartment, a diode array detector, and an automated fraction collector. Unless indicated otherwise, the mobile phase used consisted of water+0.1% formic acid and MeCN+0.1% formic acid.

Large-Scale Fermentation of S. albus J1074

Large-scale fermentation was carried out as described above. S. albus J1074 seed cultures were prepared by inoculating 50 mL of TSBY medium in a 250 mL Erlenmeyer equipped with stainless steel springs with spore stocks. The culture was grown for 2-3 days at 30° C. and 250 rpm, then diluted to a final concentration of 0.05% (w/v) in 10-20×2 L Erlenmeyer flasks each containing 200 mL R4 medium, supplemented with ivermectin (final concentration of 30 µM). The production cultures were grown at 30° C. and 250 rpm for 7 days. Then, the cells were harvested by centrifugation and the cell pellets extracted twice with ~100 mL of 1:1 MeOH/Acetone. The extracts were combined, dried in vacuo, and stored in the refrigerator until further purification. Meanwhile, the separated supernatant was extracted twice with an equal volume of ethyl acetate and the resulting organic phase dried over $Na_2SO_4$ and subsequently evaporated to dryness in vacuo.

Next HPLC-MS was carried on both the cell pellet and supernatant extracts. About 0.1 mg of dried material was resuspended in 50 µL MeOH, the suspension filtered, ~5 µL injected onto the HPLC-Qtof-MS, and subsequently eluted as described above. The analysis showed that surugamide G-J and pyrisurugamide A and B were present in both cell pellet and supernatant extracts. Acyl-surugamide A, albucyclones A-F, albuquinone A, and surugamide F2 and F3 were only found in the cell pellet extracts. The purifications of these different groups of compound sis described below.

Purification and Structural Elucidation of Surugamides G-J

Surugamides G-J were purified from 4 L fermentation of S. albus in the presence of ivermectin as described above. After fermentation, the cell pellets were harvested by centrifugation yielding ~300 g of cell paste, which was extracted twice with 2 L of 1:1 MeOH/acetone. The combined extract was evaporated to dryness in vacuo, resuspended in 40 mL MeOH, and subsequently purified on an Agilent 1260 Infinity Series Preparative HPLC equipped with a diode array detector and an automated fraction collector. The material was resolved on a preparative Luna C18 column (Phenomenex, 5 µm, 21.2×250 mm) operating at 12 mL/min with mobile phases consisting of water and MeCN (+0.1% formic acid). Upon injection, elution was carried out isocratically with 20% MeCN for 4 min, followed by a linear gradient of 20-100% MeCN over 20 min. Fractions were collected in 1 min intervals over the time range of 6-28 min. All fractions were subjected to LR-HPLC-MS analysis as described above using a 40 µL injection volume. Fractions that contained surugamides G-J were pooled, dried in vacuo, resuspended in a small volume of MeOH and further purified on a semi-preparative/analytical Agilent HPLC purified system. The sample loaded onto a semi-preparative RP Amide-C16 column (Supelco, 5 µm, 10×250 mm) operating at 2.5 mL/min with the mobile phase as above and gradients of 15-50% MeCN over 50 min followed by 50-100% MeCN over 10 min. The fractions were analyzed again by LR-HPLC-MS. Samples containing pure surugamide G-J were combined, and lyophilized to dryness. This procedure gave pure surugamides G (1.5 mg), H (1.8 mg), I (7 mg), and J (0.7 mg).

The HR-ESI-MS data obtained for these surugamides and the molecular formula are listed in Table S4. To solve their structures, comprehensive NMR data sets were acquired at the Princeton University Department of Chemistry NMR Facilities. All 1D/2D NMR spectra were collected in MeOH-d4 in the triple resonance cryoprobe of an A8 Avance III HD 800 MHz NMR spectrometer (Bruker). NMR data were analyzed in MestReNova (MestreLab Research).

Purification and Structural Elucidation of Pyrisurugamides A and B

A similar procedure was used to purify pyrisurugamides A and B, as that described for surugamides G-J above. Upon extraction of cell pellets and preparative HPLC (as described above), fractions containing pyrisurugamides A and B, as judged by HPLC-MS, were combined, dried in vacuo and resuspended in MeOH. They were purified further on a semi-preparative RP Amide-C16 column (Supelco, 5 μm, 10×250 mm) with a flow rate of 2.5 mL/min and isocratic elution with 42% MeCN for 30 min followed by a linear gradient of 42-100% MeCN over 18 min. Fractions containing pyrisurugamide A were purified further on a Phenomenex Luna C18 column (5 μm, 4.6×250 mm) at a flow rate of 1 mL/min and a gradient of 44° % MeCN over 30 min and 44-100% MeCN over 8 min.

This procedure gave 0.3 mg of pure pyrisurugamide A, which was characterized by HR-MS and comprehensive NMR analysis at 800 MHz in MeOD-d4.

Pyrisurugamide B was not obtained in yields sufficient for NMR analysis. Instead, its structure was inferred from HR-MS and HR-tandem-MS using a range of collision energies (25, 35, 45, and 55 V) on a HPLC-Qtof-MS. See FIG. S14.

Purification and Structural Elucidation of Albucyclones A-F

To purify albucyclones A-F, 8 L of *S. albus* J1074 were cultured in the presence of ivermectin as described above for surugamides and pyrisurugamides. After fermentation, the cell pellets were removed by centrifugation (RT, 8000 g, 30 min) on a Beckman-Coulter Avanti J26-XP centrifuge, and the supernatant extracted twice with an equal volume of ethyl acetate. The organic layers were combined, treated with $Na_2SO_4$, and then evaporated to dryness in vacuo. The residue was dissolved in 35 mL MeOH and purified by HPLC using a preparative Luna C18 column (Phenomenex, 5 μm, 21.2×250 mm) operating at 12 mL/min with the same elution program as sued for surugamides: 20% MeCN for 4 min, followed by a gradient from 20-100% MeCN over 20 min. Fractions were collected in 1 min intervals from 4-30 min and monitored by HR-HPLC-MS for presence of albucyclones (40 μL injection). Those containing acyl-surugamide A, albuquinone, and surugamide F were collected, dried and stored at 4° C. until further purification. Factions containing albucyclones were pooled, dried and further resolved on a semi-preparative RP Amide-C16 column (Supelco, 5 μm, 10×250 mm) operating at 2.5 mL/min. Upon injection, samples were eluted isocratically (40% MeCN for 30 min) followed by 40-100% linear gradient over 8 min. with same linear gradient step: 40% B to 58% B (0-30 min), 100% B (30-38 min) (A, Milli-Q H2O; B, MeCN). For final purifications, fractions containing albucyclones were inject on an analytical Luna C18 column (Phenomenex, 5 μm, 4.6×250 mm) and eluted as described above for the semi-preparative column, but using a flow-rate of 1 mL/min. This procedure yielded pure albucyclone A (1.8 mg), B (0.4 mg), C (0.5 mg), D (0.6 mg), E (0.5 mg) and F (1.5 mg). They were characterized by HR-MS, HR-MS/MS and 1D/2D NMR.

Purification and Structural Elucidation of Acyl-Surugamide A

Dried fractions containing acyl-surugamide A (from the preparative Luna C18 column, see last paragraph) were dissolved in MeOH and purified further on semi-preparative Luna C18 column (Phenomenex, 5 μm, 10×250 mm) with a flow-rate of 2.5 mL/min. Elution was carried out with 30% MeCN over 5 min, followed by linear gradients consisting of 30-40% over 26 min and 40-100% over 8 min. Fractions containing acyl-surugamide A, as detected by HR-HPLC-MS, were pooled and dried yielding 0.6 mg of pure material. Subsequently, HR-MS and 1D/2D NMR was carried out for structural elucidation.

Purification and Structure Elucidation of Albuquinone A

Dried fractions containing albuquinone A (from preparative Luna C18 column, see "Purification and structural elucidation of albucyclones A-F") were dissolved in MeOH and purified further on a semi-preparative RP Amide-C16 column (Supelco, 5 μm, 10×250 mm). Elution was carried out with a flow-rate of 2.5 mL/min and linear gradients consisting of 12-19% MeCN over 27 min, and 19-100% MeCN over 7 min. This procedure yielded 0.3 mg pure albuquinone A, which was subsequently characterized by HR-MS and 1D/2D NMR.

Purification and Structural Elucidation of Surugamides F2 and F3

Dried fractions containing surugamide F analogs (from preparative Luna C18 column, see "Purification and structural elucidation of albucyclones A-F") were dissolved in MeOH and purified further on a semi-preparative RP Amide-C16 column (Supelco, 5 μm, 10×250 mm) operating at 2.5 mL/min. Elution was performed with a linear gradient of 30-40% MeCN over 30 min and 40-100% MeCN over 8 min. Samples containing surugamide F variants, as determined by HR-MS/MS, were resolved further on an analytical Luna C18 column (Phenomenex, 5 μm, 4.6×250 mm). Elution was carried out with a flow-rate of 1 mL/min and a linear gradient of 40-44% MeCN over 30 min, followed by 44-100% MeCN over 8 min. This procedure gave pure surugamide F (0.5 mg), surugamide F2 (<0.2 mg) and surugamide F3 (<0.2 mg). The structures of surugamide F2 and F3 were elucidated using targeted HR-tandem-MS with varying collision energies (25, 35, 45, 55 V) on the Agilent HPLC-Qtof-MS instrument described above. Fragment ions form the various runs were combined and analyzed in MassHunter software. These unambiguously revealed the linear sequence of surugamide F2. In the case of surugamide F3, we could not distinguish between Ile and Leu at position 7 of the linear peptide (see FIG. 6F).

Antibiotic and Cathepsin B Inhibition Assays

*Bacillus subtilis* 168, *E. coli* K 12, *Pseudomonas aeruginosa* PAO1, *Enterococcus faecalis* OG1RF, *Staphylococcus aureus* Newman, *Saccharomyces cerevisiae* and *Saccharomyces pombe* were used for antibiotic assays. *B. subtilis* (30° C.), *E. coli* (37° C.), *P. aeruginosa* (30° C.), and *E. faecalis* (37° C.) were cultured in LB medium at the temperatures indicated. *S. aureus* was cultured in Brain-Heart-Infusion (BHI) medium at 37° C. *S. cerevisiae* and *S. pombe* were grown at 25° C. in YPM medium (0.5% yeast extract, 0.3% peptone, 2.5% mannitol), and YES medium (0.5% yeast extract, 3% glucose, 225 mg/L leucine, 225 mg/L histidine, 225 mg/L adenine, 225 mg/L uracil), respectively. The assays were carried out in accordance with the 2003 guidelines of the Clinical and Laboratory Standards Institute (CLSI) using the microtiter method. Briefly, microbial seed cultures were initiated by inoculating 3 mL of the indicated medium each strain and by growing these overnight at the indicated temperatures. Each culture was then diluted to an initial $OD_{600\ nm}$ of 0.02 in 100 μL volume per well in a 96-well plate, which gave an inoculum of ~$5\times10^5$ to $5\times10^6$ cells. The wells contained varying concentrations of the compounds tested: 0, 0.02, 0.04, 0.1, 0.2, 0.4, 1, 2, 4, 10, 20, 40, 100 μM final concentration. Assays were set-up in triplicates. The plates were then incubated at the temperatures listed above without shaking and $OD_{600\ nm}$ determined after 16 h (bacteria) or 40 h (yeast). The compounds used for antibiotic assays included surugamide, pyrisurugamide A, albuquinone, acyl-surugamide A, albucyclones.

Cathepsin B inhibition assays were carried as previously reported using the Cathepsin B Inhibition assay kit (Sigma-Aldrich). The fluorescence-based assays was conducted in a final volume of 50 μL according to manufacturer instructions. Fluorescence emission was determined in a microtiter plate in kinetic mode (1 read per minute for 1 h) using a BioTek H1MF plate reader and $A_{ex}$~400/$A_{cm}$~505 nm. $IC_{50}$ values were subsequently calculated according to instructions.

TABLE 3

Primer and qPCR parameters used for creating mutants and performing RT-qPCR.

| Primer Sequences | Primer Function |
| --- | --- |
| 5'-AAGCTTAGACGACCACCTTCGCCGTCTGC-3'<br>5'-AAGCTTTAGACGGACGGGACGGCGTGCAGC-3' | Cloning surA fragments for making surA::apr mutant |
| 5'-AAGCTTACGAGACCCTGCGGACCGTCTTCC-3'<br>5'-AAGCTTTCGTGCACCACCTGCACCGGCTGC-3' | Cloning surB fragments for making surB::apr mutant |
| 5'-TTCTTCGTCAACACCCTGGTGCTGCGGCAGCAGGTGCCGGATTCCGGGGATCCGTCGACC-3'<br>5'-GACCGGGTGGTCGGTGAGGCTGAGGATGTCGTGGGCGATCTTGTAGGCTGGAGCTGCTTC-3' | Cloning Apr$^R$ gene cassette for surA::apr |
| 5'-AGATCAGCCACACCCTGATCCCGCCGACGGTCCTCGCCAGATTCCGGGGATCCGTCGACC-3'<br>5'-CGAGGCTGAAGAAGTTGTCCCGGGTGCCGACACGTTCCACCTGTAGGCTGGAGCTGCTTC-3' | Cloning Apr$^R$ gene cassette for surB::apr |
| 5'-ACTCTAGACTGAAGTTCTCCGGGCCCACGAC-3'<br>5'-GTCGTACGGTCACCATCCTCTAGTCAAGCTTGCACAGCTTCAATCTATCTG-3' | Cloning the left arm of surR::apr knock out plasmid |
| 5'-CAAGCTTGACTAGAGGATGGTGACCGTACGAC-3'<br>5'-GCTCTAGATGCCTCGCCTGCCTCACCAGACTC-3' | Cloning the right arm of surR::apr knock out plasmid |
| 5'-AGTAAGCTTCCACCGACTATTTGCAACAGT-3'<br>5'-ACCAAGCTTCGGGGTCATTATAGCGATTTT-3' | Generating the fused surR::apr fragment |
| 5'-ATCATCACGCGCGAGCTGAGC-3'<br>5'-CGAGGACGAGGAGTTTCG-3' | Primers for validation of the genotype of surA::apr mutant |
| 5'-AGATCAGCCACACCCTGATCC-3'<br>5'-TGAAGAAGTTGTCCCGGGTGC-3' | Primers for validation of the genotype of surB::apr |
| 5'-GGATCCATCAGTGCCATGGGGAGCTTCC-3'<br>5'-TTGCTCACCATTGCGTCCCTGCGCCACTGC-3' | Cloning left arm of surE::eGFPx3 knockout plasmid |
| 5'-GAATTCATGTTCCAGGATGAGCGGTCG-3'<br>5'-AAGCTTTCCAGGAACCAGAGCCGTTCCTGC-3' | Cloning right arm of surE::eGFPx3 knockout plasmid |
| 5'-AGGGGACGCAATGGTGAGCAAGGGCGAGG-3'<br>5'-GAATTCTCACTTGTACAGCTCGTCCATG-3' | Generating the fused surE::eGFPx3 fragment |
| 5'-TTTCCGCTGCTGCTGAAGCTG-3'<br>5'-TCGAGTTCGCGGTAGGTCAGG-3' | Primers for validation of the genotype of surE::eGFPx3 |
| 5'-TTGCTCACCATTGCGTCCCTGCGCCCAC-3'<br>5'-AGGGGACGCAATGGTGAGCMGGGCGAGG-3' | Cloning Psur-eGFPx3 for pSET152 to generate attB::Psur-eGFPx3 |
| 5'-ATCATATGATGGTGAGCAAGGGCGAGGAG-3'<br>5'-AAGAATTCTCACTTGTACAGCTCGTCCATG-3' | Cloning eGFP into pIB139 |

TABLE 3-continued

Primer and qPCR parameters used for creating mutants and performing RT-qPCR.

| | |
|---|---|
| 5'-ACAATTGCAGCTCAAGGAGGATCCATCATGGTGAGCAA GGGCGAGGAG-3'<br>5'-AAGAATTCTCACTTGTACAGCTCGTCCATG-3' | Amplifying eGFP with RBS site |
| 5'-ATAAGCTTATGAACAAAGGTGTAATGCG-3'<br>5'-AATCTAGATCAGGTCAGCACGGTCATG-3' | Cloning xylE for creating the Psur-xylE fragment for pSET152 |
| 5'-GCTTCTAGAGGGCGCGCTGCTCAACGTGA-3'<br>5'-ACAAGCTTGCGTCCCCTCCGCCCAGTGCAAC-3' | Cloning Psur for creating the Psur-xylE fragment for pSET152 |
| 5'-ATCATATGATGAAAAAAGGAGTTATGCG-3'<br>5'-AAGAATTCTCAGGTCAGCACGGTCATG-3' | Cloning xylE downstream of $P_{ermE}$ to make $P_{ermE}$-xylE |

| RT-qPCR Primer Sequences | Gene | A/E Temp (° C.) | Amplicon length (bp) |
|---|---|---|---|
| 5'-CAAGACCGTCAAGGTGCTCT-3'<br>5'-GAGCCGAGATGATGACCTTC-3' | XNR4919 (gapdh) | 64.4 | 158 |
| 5'-GAGAACTACCCGGACAACGA-3'<br>5'-GGGTCGTAGGAGAGGTCCAG-3' | XNR3449 (surA) | 64.4 | 146 |
| 5'-GACGAGACCCTGTCTTACGC-3'<br>5'-AGTACGGTCAGCCACTCGAC-3' | XNR3447 (surC) | 64.4 | 134 |
| 5'-AGGTCCCGATCTACCAGCA-3'<br>5'-GTAGGCCTTGTTGACGGTGT-3' | XNR3452 (surR) | 64.4 | 143 |

Those in the art will understand that a number of variations may be made in the disclosed embodiments, all without departing from the scope of the invention, which is defined solely by the appended claims.

The invention claimed is:

1. A method for activating silent biosynthetic gene clusters in actinomycete bacteria, the method comprising the steps of:
providing at least one actinomycete bacterial cell, wherein the bacterial cell contains at least one of a promoter from a targeted gene cluster that is silent or lowly-expressed fused to at least one reporter gene at a neutral site or the promoter fused to at least one reporter gene at a site within the targeted gene cluster;
exposing the bacterial cell to test compounds from a small molecule library;
measuring the expression of the at least one reporter gene at a first point in time;
measuring the expression of the at least one reporter gene at a second point in time;
identifying activation of gene clusters by determining whether the expression of the at least one reporter gene has increased by more than a threshold amount from the first point in time to the second point in time.

2. The method of claim 1, wherein the actinomycete bacterium is from the genus *Streptomyces* or *Saccharopolyspora*.

3. The method of claim 1, wherein the threshold amount is a 2.5-fold induction of the reporter gene, or more.

4. The method of claim 1, wherein the at least one reporter gene is eGFP.

5. The method of claim 4, wherein the at least one reporter gene comprises at least three copies of eGFP.

6. The method of claim 1, wherein the neutral site is attB.

7. The method of claim 1, further comprising utilizing a positive and negative control for expression of the promoter-reporter fusion.

8. The method of claim 1, further comprising utilizing a second actinomycete bacterial cell that is a different strain than the strain of the at least one actinomycete bacterial cell to subject the different strain to one or more compounds of the small molecule library.

9. The method of claim 1, further comprising utilizing a second actinomycete bacterial cell, and any silent biosynthetic gene cluster in that actinomycete, to subject the second actinomycete bacterial cell to one or more compounds of the small molecule library.

* * * * *